US008679315B2

(12) United States Patent
Manaresi et al.

(10) Patent No.: US 8,679,315 B2
(45) Date of Patent: Mar. 25, 2014

(54) METHOD AND APPARATUS FOR CHARACTERIZING AND COUNTING PARTICLES, IN PARTICULAR, BIOLOGICAL PARTICLES

(75) Inventors: Nicolò Manaresi, Via Santo Stefano (IT); Roberto Guerrieri, Via Calari (IT); Gianni Medoro, Via della Badia (IT)

(73) Assignee: Silicon Biosystems S.p.A., Bologna (IT)

( * ) Notice: Subject to any disclaimer, the term of this patent is extended or adjusted under 35 U.S.C. 154(b) by 1377 days.

(21) Appl. No.: 12/091,438

(22) PCT Filed: Mar. 22, 2006

(86) PCT No.: PCT/IB2006/000636
§ 371 (c)(1),
(2), (4) Date: Oct. 10, 2008

(87) PCT Pub. No.: WO2007/049103
PCT Pub. Date: May 3, 2007

(65) Prior Publication Data
US 2009/0218223 A1 Sep. 3, 2009

(30) Foreign Application Priority Data

Oct. 26, 2005 (IT) .............................. BO2005A0646

(51) Int. Cl.
B01D 57/02 (2006.01)
(52) U.S. Cl.
USPC ........................................ 204/547; 204/643
(58) Field of Classification Search
USPC ................................................ 204/547, 643
See application file for complete search history.

(56) References Cited

U.S. PATENT DOCUMENTS 5,252,493 A 10/1993 Fujiwara et al.
5,279,493 A 1/1994 Halder
(Continued)

FOREIGN PATENT DOCUMENTS

DE 3931851 4/1992
DE 10203636 2/2004
(Continued)

OTHER PUBLICATIONS

Altomare et al., Levitation and movement of human tumor cells using a printed circuit board device based on software-controlled dielectrophoresis, Biotechnol. Bioeng., 82(4):474-9 (2003).

(Continued)

Primary Examiner — J. Christopher Ball
(74) Attorney, Agent, or Firm — Marshall, Gerstein & Borun LLP

(57) ABSTRACT

The present invention relates to a method and an apparatus for the characterization and/or the counting of particles by means of non uniform, time variable force fields and integrated optical or impedance meter sensors. The force fields can be of positive or negative dielectrophoresis, electrophoresis or electro-hydrodynamic motions, characterized by a set of stable equilibrium points for the particles (solid, liquid or gaseous); the same method is suitable for the manipulation of droplets (liquid particles) by exploiting effects known to the international scientific community with the name of Electrowetting on dielectric. The aim of the present invention is to act on the control of the position of each particle which is present in the sample, for the purpose of displacing such particles in a deterministic or statistical way, in order to detect their presence with the integrated optical or impedance meter sensors and/or characterize their type, for the purpose of counting or manipulating them in an efficient way.

24 Claims, 13 Drawing Sheets

(56) References Cited

U.S. PATENT DOCUMENTS

| | | | |
|---|---|---|---|
| 5,888,730 A | 3/1999 | Gray et al. | |
| 5,945,281 A | 8/1999 | Prabhu | |
| 6,149,789 A | 11/2000 | Benecke et al. | |
| 6,203,683 B1 | 3/2001 | Austin et al. | |
| 6,264,815 B1 | 7/2001 | Pethig et al. | |
| 6,294,063 B1 | 9/2001 | Becker et al. | |
| 6,824,664 B1 | 11/2004 | Austin et al. | |
| 6,830,729 B1 | 12/2004 | Holl et al. | |
| 6,875,329 B2 | 4/2005 | Washizu et al. | |
| 6,888,721 B1 | 5/2005 | Moghaddam et al. | |
| 6,911,132 B2 | 6/2005 | Pamula et al. | |
| 6,977,033 B2 | 12/2005 | Becker et al. | |
| 7,147,763 B2 | 12/2006 | Elrod et al. | |
| 7,250,933 B2 | 7/2007 | De Boer et al. | |
| 7,307,328 B2 | 12/2007 | Meyer et al. | |
| 7,488,406 B2 | 2/2009 | Hughes et al. | |
| 7,641,779 B2 | 1/2010 | Becker et al. | |
| 8,216,513 B2 | 7/2012 | Becker et al. | |
| 8,349,160 B2 | 1/2013 | Medoro et al. | |
| 8,388,823 B2 | 3/2013 | Manaresi et al. | |
| 2002/0031838 A1 | 3/2002 | Meinhart et al. | |
| 2002/0036139 A1 | 3/2002 | Becker et al. | |
| 2002/0070114 A1 | 6/2002 | Miles | |
| 2002/0125138 A1* | 9/2002 | Medoro | 204/547 |
| 2002/0132316 A1 | 9/2002 | Wang et al. | |
| 2003/0044832 A1 | 3/2003 | Blankenstein | |
| 2003/0047456 A1* | 3/2003 | Medoro | 204/547 |
| 2003/0073110 A1 | 4/2003 | Aritomi et al. | |
| 2004/0011652 A1 | 1/2004 | Bressler | |
| 2004/0055891 A1 | 3/2004 | Pamula et al. | |
| 2004/0058450 A1 | 3/2004 | Pamula et al. | |
| 2004/0063196 A1 | 4/2004 | Muller et al. | |
| 2004/0159546 A1 | 8/2004 | Zhang et al. | |
| 2004/0191789 A1 | 9/2004 | Manaresi et al. | |
| 2004/0209354 A1 | 10/2004 | Mathies et al. | |
| 2004/0229210 A1 | 11/2004 | Sabry et al. | |
| 2005/0014146 A1 | 1/2005 | Manaresi et al. | |
| 2005/0214736 A1 | 9/2005 | Childers et al. | |
| 2006/0051775 A1 | 3/2006 | Bianchi | |
| 2006/0086309 A1 | 4/2006 | Manger et al. | |
| 2006/0139638 A1 | 6/2006 | Muller et al. | |
| 2006/0177815 A1 | 8/2006 | Soh et al. | |
| 2006/0223178 A1 | 10/2006 | Barber et al. | |
| 2006/0228749 A1 | 10/2006 | Wang et al. | |
| 2007/0026024 A1 | 2/2007 | Toner et al. | |
| 2007/0026415 A1 | 2/2007 | Fuchs et al. | |
| 2007/0051412 A1 | 3/2007 | Heath et al. | |
| 2007/0059683 A1 | 3/2007 | Barber et al. | |
| 2007/0172903 A1 | 7/2007 | Toner et al. | |
| 2007/0250301 A1 | 10/2007 | Vaisberg et al. | |
| 2008/0058991 A1 | 3/2008 | Lee et al. | |
| 2008/0246489 A1 | 10/2008 | Coster et al. | |
| 2008/0264068 A1 | 10/2008 | Nakasuka et al. | |
| 2009/0205963 A1 | 8/2009 | Medoro et al. | |
| 2009/0218223 A1 | 9/2009 | Manaresi et al. | |
| 2010/0035292 A1 | 2/2010 | Levhenko et al. | |
| 2010/0248285 A1 | 9/2010 | Manaresi | |
| 2010/0331205 A1 | 12/2010 | Medoro | |
| 2012/0071335 A1 | 3/2012 | Manaresi et al. | |
| 2012/0091001 A1 | 4/2012 | Manaresi et al. | |
| 2012/0184010 A1 | 7/2012 | Medoro et al. | |
| 2013/0118903 A1 | 5/2013 | Becker et al. | |

FOREIGN PATENT DOCUMENTS

| | | |
|---|---|---|
| DE | 19500660 | 12/2007 |
| EP | 1145766 | 8/2007 |
| EP | 1304388 | 2/2008 |
| EP | 1179585 | 7/2008 |
| JP | 58211272 A | 12/1983 |
| JP | 2002311461 A | 10/2002 |
| JP | 2002536167 A | 10/2002 |
| JP | 2003121886 A | 4/2003 |
| JP | 2003202604 A | 7/2003 |
| JP | 2004000935 A | 1/2004 |
| JP | 2005501296 A | 1/2005 |
| JP | 2005507997 A | 3/2005 |
| JP | 2007017163 A | 1/2007 |
| JP | 2008533487 A | 8/2008 |
| WO | WO-91/07660 A1 | 5/1991 |
| WO | WO-91/08284 | 6/1991 |
| WO | WO-98/04355 | 2/1998 |
| WO | WO-99/17883 | 4/1999 |
| WO | WO-00/28313 | 5/2000 |
| WO | WO-00/47322 A2 | 8/2000 |
| WO | WO-00/69565 A1 | 11/2000 |
| WO | WO-02/12896 | 2/2002 |
| WO | WO-03/014739 | 2/2003 |
| WO | WO-03/035895 A2 | 5/2003 |
| WO | WO-03/045556 | 6/2003 |
| WO | WO-2004/030820 A2 | 4/2004 |
| WO | WO-2004/071668 | 8/2004 |
| WO | WO-2005/060432 | 7/2005 |
| WO | WO-2005/098395 | 10/2005 |
| WO | WO-2006/003214 A2 | 1/2006 |
| WO | WO-2006008602 A2 | 1/2006 |
| WO | WO-2006/018849 A2 | 2/2006 |
| WO | WO-2007/010367 A2 | 1/2007 |
| WO | WO-2007/049103 | 5/2007 |
| WO | WO-2007/049120 | 10/2007 |
| WO | WO-2007/110739 A2 | 10/2007 |
| WO | WO-2007/116312 A2 | 10/2007 |
| WO | WO-2007/147018 A1 | 12/2007 |
| WO | WO-2007147076 A2 | 12/2007 |
| WO | WO-2008/112274 A2 | 9/2008 |
| WO | WO-2008/131035 A2 | 10/2008 |
| WO | WO-2009/022222 | 2/2009 |

OTHER PUBLICATIONS

Cheung et al., Impedance spectroscopy flow cytometry: on-chip label-free cell differentiation, Cytometry Part A, 65A(2):124-32 (2005).

Final office action, U.S. Appl. No. 12/091,367, mail date Nov. 1, 2011.

Gascoyne et al., Dielectrophoresis-based programmable fluidic processors, Lab Chip, 4:299-304 (2004).

Gascoyne et al., Particle separation by dielectrophoresis, Electrophoresis, 23(13): 1973-83 (2002).

Green et al., Ac Electrokinetics: a survey of sub-micrometre particle dynamics, J. Phys. D: Appl. Phys., 33:632-41 (Dec. 10, 1999).

Hughes, Strategies for dielectrophoretic separation in laboratory-on-a-chip systems, Electrophoresis, 23(16): 2569-82 (2002).

International Preliminary Report on Patentability for PCT/IB2006/000636, dated Apr. 29, 2008.

International Preliminary Report on Patentability for PCT/IB2006/001984, dated Dec. 3, 2007.

International Preliminary Report on Patentability for PCT/IB2006/002965, dated Apr. 29, 2008.

International Preliminary Report on Patentability for PCT/IB2007/000751, dated Sep. 30, 2008.

International Preliminary Report on Patentability for PCT/IB2010/000615, dated Sep. 20, 2011.

International Search Report and Written Opinion for PCT/IB2006/000636, dated Sep. 8, 2006.

International Search Report and Written Opinion for PCT/IB2006/001984, dated Feb. 27, 2007.

International Search Report and Written Opinion for PCT/IB2006/002965, dated Jun. 15, 2007.

International Search Report and Written Opinion for PCT/IB2007/000751, dated Nov. 16, 2007.

International Search Report and Written Opinion for PCT/IB2010/000615, mailing date Aug. 26, 2010.

Jones, An electromechanical interpretation of electrowetting, J. Micromech. Microeng., 15(6):1184-7 (2005).

Manaresi et al., A CMOS chip for individual cell manipulation and detection, IEEE Journal of Solid-State Circuits, 38 (12):2297-305 (2003).

(56) References Cited

OTHER PUBLICATIONS

Medoro et al., A lab-on-a-chip for cell detection and manipulation, IEEE Sensors Journal, 3(3):317-25 (2003).

Medoro et al., A lab-on-a-chip for cell separation based on the moving-cages approach, Proceedings of the 16th Conference on Solid State Transducers, pp. 500-501 (Sep. 15, 2002).

Medoro et al., Dielectrophoretic cage-speed separation of bio-particles, Sensors, Proceedings of the IEEE Vienna, Austria, Oct. 24-27, 2004, pp. 76-79.

Nieuwenhuis et al., Near-field optical sensors for particle shape measurements, Sensors Journal IEEE, 3(5):646-51 (2003).

Nonfinal office action, U.S. Appl. No. 12/091,367, mail date Mar. 25, 2011.

Nonfinal office action, U.S. Appl. No. 12/294,860, mail date Jan. 27, 2012.

Nonfinal office action, U.S. Appl. No. 11/724,697, notification date Jun. 7, 2011.

Nonfinal office action, U.S. Appl. No. 11/724,697, notification date Sep. 23, 2010.

O'Hara et al., Ratcheting electrophoresis microchip (REM) for programmable transport and separation of macromolecules, Proceedings of the International Mechanical Engineering Congress and Exposition, 3:619-28 (2001).

Office Action, U.S. Appl. No. 11,724,697, notification date Jan. 27, 2012.

Petersson et al., Carrier medium exchange through ultrasonic particle switching in microfluidic channels, Anal. Chem., 77:1216-21 (2005).

Pethig et al., Enhancing traveling-wave dielectrophoresis with signal superposition, IEEE Eng. Med. Biol. Mag., 22(6):43-50 (2003).

International Preliminary Report on Patentability for corresponding International Application No. PCT/EP2005/053235, mailing date Jan. 9, 2007.

International Search Report and Written Opinion for corresponding International Application No. PCT/EP2005/053235, mailing date May 2, 2006.

Rousselet et al., Directional motion of brownian particles induced by a periodic asymmetric potential, Nature, 370(6489):446-8 (1994).

Berthier et al., NSTI Nanotech 2005, vol. 1 (2005), www.nsti.org.

Fiedler et al., Electrocasting formation and structuring of suspended microbodies using A.C. generated field cages, Microsystem Technologies, Berlin, Germany, pp. 1-7 (Dec. 1, 1995).

Fuhr et al., Positioning and manipulation of cells and microparticles using miniturized electric field traps and travelling waves, Sensors and Materials, 7(2):131-46 (1995).

Milner et al., Dielectrophoretic classification of bacteria using differential impedance measurements, Electronics Letters, 34(1):66-8 (1998).

Ohta et al., Tech. Dig. of the Solid State Sensor, Actuator and Microsystems, Workshop, pp. 216-219 (2004).

Schnelle et al., Three-dimensional electric field traps for manipulation of cells—calculation and experimental verfication, Biochem. Biophys. Acta, 1157(2):127-40 (1993).

Suehiro, The dielectrophoretic movement and positioning of a biological cell using a three-dimensional grid electrode system, J. Phys. D: Appl. Phys., 31:3298-305 (1998).

Bonci et al., The *miR-15a-miR-16-1* cluster controls prostate cancer by targeting multiple oncogenic activities, Nat. Med., 14:1271-7 (2008).

Final office action, U.S. Appl. No. 11/724,697, mail date Jan. 27, 2012.

Fuchs et al., Electronic sorting and recovery of single live cells from microlitre sized samples, Lab Chip, 6:121-6 (2006).

International Preliminary Report on Patentability for corresponding International Application No. PCT/IB2009/007316, Jan. 21, 2011.

International Search Report in PCT/IB2008/002873, dated Aug. 3, 2009.

Klein et al., Comparative genomic hybridization, loss of heterozygosity, and DNA sequence analysis of single cells, Proc. Natl. Acad. Sci. USA, 96(8):4494-9 (1999).

Nagrath et al., Isolation of rare circulating tumour cells in cancer patients by microchip technology, Nature, 450(7173):1235-9 (2007).

Nonfinal office action, U.S. Appl. No. 11/996,068, mail date Jan. 4, 2013.

Nonfinal office action, U.S. Appl. No. 12/740,170, mail date Jun. 5, 2013.

Reichle et al., Combined laser tweezers and dielectric field cage for the analysis of receptor-ligand interactions on single cells, Electrophoresis, 22(2):272-82 (2001).

Romani et al., Capacitive sensor array for localization of bioparticles in CMOS lab-on-a-chip, Proc. Int. Solid State Circuit Conference, 1:224-5 (2004).

Stoecklein et al., Direct genetic analysis of single disseminated cancer cells for prediction of outcome and therapy selection in esophageal cancer, Cancer Cell, 13:441-53 (2008).

Zieglschmid et al., Detection of disseminated tumor cells in peripheral blood, Crit. Rev. Clin. Lab. Sci., 42(2):155-96 (2005).

English translation of Office Action, Japanese patent application No. 2012-167396 (Aug. 2, 2013).

de Bono et al., Circulating tumor cells predict survival benefit from treatment in metastatic castration-resistant prostate cancer, Clin. Cancer Res., 14(19):6302-9 (2008).

\* cited by examiner

METHOD AND APPARATUS FOR CHARACTERIZING AND COUNTING PARTICLES, IN PARTICULAR, BIOLOGICAL PARTICLES

CROSS REFERENCES TO RELATED APPLICATIONS

This application is a U.S. National Phase Application under 35 USC §371 of International Application PCT/IB2006/000636 filed on 22 Mar. 2006 designating the United States, which claims priority to Italian Application No. BO2005A000646, filed Oct. 26, 2005. Priority to each of the foregoing PCT and Italian national applications is claimed herein under all applicable laws and provisions, and each of said priority applications is incorporated by reference in its entirety.

TECHNICAL FIELD

The present invention relates to methods and apparatus for the characterization and/or the counting of particles. The invention mainly finds an application in the implementation of biological protocols on single cells.

STATE OF THE ART

The PCT/WO 00/69565 patent application to G. Medoro describes an apparatus and a method for the manipulation and the detection of particles through the use of closed dielectrophoretic potential cages. The method described teaches how to control the position of each particle independently of all the others in a two-dimensional space. The force used for trapping in suspension the particles is the negative dielectrophoresis. The individual control on the manipulation operations takes place through the programming of memory elements and circuits associated with each element of an array of electrodes and sensors integrated within a same substrate. However, the fixed spatial "noise" bound to the dispersion of the characteristics of the sensors (technically known as "Fixed-Pattern-Noise") severely limits the reliability of the sensors themselves in the detection of cells. The patent reports the use of optical and/or impedance meter sensors. Even by subtracting a reference image for the compensation of the variations on the gain of the sensors, the result is not completely reliable, since other factors, such as for example spatial variations of the illumination (for the optical sensors) or the conductivity of the liquid (for the impedance meter sensors), are not compensated. The U.S. Pat. No. 6,294,063, Becker et al, discloses a method and an apparatus for the manipulation of packages of solid, liquid or gaseous biological material through a distribution of programmable forces. The patent also mentions the use of sensors. But also in this case, there is the problem of the Fixed-Pattern-Noise.

Another known method for the manipulation of liquid particles (droplets) is the Electro-wetting on Dielectric (EWOD), described in T. B. Jones, *Journal of Micromechanics and Microengineering*, 15 (2005) 1184-1187. In this case, an electric field exerted by electrodes provided on a substrate allows the propulsion of a droplet surrounded by a gaseous phase in a direction controlled by the sequence of energized electrodes. Devices based on this principle can be made by including a lid (also the same coated with a dielectric) as taught by the patent application US 2004/0058450A1 to Pamula et al., or also simply a wire, called "chain", which establishes the electric contact with the droplets above the substrate. J Berthier et al., *NSTI Nanotech* 2005, www.nsti.org, vol. 1, 2005.

A further force for the manipulation of particles is the viscous friction force generated by electro-hydrodynamic (EHD) flows, such as the electro-thermal flows (ETF) or the AC electro-osmosis. In N G. Green, A. Ramos and H. Morgan, *J. Phys. D: Appl. Phys.* 33 (2000), the EHDs are used for displaying particles. For example, PCT WO 2004/071668 A1 describes an apparatus for concentrating particles on some electrodes, by exploiting the aforesaid electro-hydrodynamic flows.

In "Impedance Spectroscopy Flow Cytometry: On-Chip Label-Free Cell Differentiation", Cytometry Part A 65A: 124-132 (2005), Cheung K, Gawad S, Renuad P, an impedance differential sensor integrated on a microchip is used for differentiating particles in a flow.

In "Near-Field Optical Sensors for Particle Shape Measurements", IEEE Sensor Journal, vol. 3, No. 5, October 2003, pp. 646-651, a chip for the detection of the particle shape based on arrays of integrated sensors (photodiodes) is described. However, the movement of the particles is operated by a liquid flow, which requires for example a pump or other analogous mechanisms, and therefore it is impossible to accurately control the position of the particles to be analyzed.

In the Italian patent application BO2005A000481, Medoro et al, some methods for manipulating particles with arrays of electrodes and some methods and apparatus for their detection are reported, which have however limitations similar to the patent PCT/WO 00/69565 already mentioned, as for the ability of differentiating the different cells.

Finally, in the International patent application No. PCT/IT02/00524, a method wherein first biological entities are recognized through second biological entities having the capability of binding to the first one (or vice versa) is described, where the first biological entities are immobilized on a surface defined by a matrix of first electrodes at least partly selectively activable and addressable, arranged faced towards at least a second electrode, and are contacted with the second biological entities displaced through dielectrophoresis cages; the bonding interaction, if any, between at least a part of the first and the second biological entities is preferably detected by exciting fluorophores groups bound to the second biological entities with radiations at a first frequency and detecting the fluorescence emission at a second frequency through optical sensors integrated within the electrodes. Therefore, there is again the problem of eliminating the "noise" connected with the optical detection ("Fixed Pattern Noise").

SUMMARY OF THE INVENTION

The aim of the present invention is to provide a method and an apparatus for carrying out the characterization and/or the counting of particles of any type, which is free from the drawbacks described and which, in particular, allows a precision manipulation of the particles to be obtained, being at the same time substantially insensitive to the drawback of the Fixed-Pattern-Noise.

It is particularly an aim of the present invention to act on the control of the position of each particle present in the sample, for the purpose of displacing such particles in a deterministic or statistical way, for detecting their presence and/or characterizing their type with integrated optical and/or impedance meter sensors.

Here and in the following, by the terms "particles" or "particle", natural or artificial, micrometric or nanometric entities are intended, such as cells, sub-cellular components, viruses, liposomes, niosomes, microballs (microspheres) and nanoballs, or also smaller entities, such as macro-molecules, proteins, DNA, RNA, etcetera, as well as drops of an fluid immiscible in a suspension medium, for example oil-in-water or water-in-oil, or also drops of liquid in a gas (such as water-in-air) or, still, gas bubbles in a liquid (such as air-in-water).

Sometimes, the term cell will be used, but where not otherwise specified it should be intended as a non limiting example of the use for the detection and characterization of particles in the widest sense above described.

The present invention therefore relates to a method and an apparatus for the characterization and/or the counting of particles, as above specified, according to the claims 1, 3, 5, 9, 11, 20, 22.

In particular, non uniform, time variable force fields and integrated optical sensors are used. The force fields can be of positive or negative dielectrophoresis, electrophoresis or electro-hydrodynamic motions, characterized by a set of stable equilibrium points for the particles (solid, liquid or gaseous); the same method is adapted to the manipulation of droplets (liquid particles) by exploiting effects known to the international scientific community by the name of Electrowetting on dielectric.

In this way, the restrictions of the known art are overcome by the present invention.

The implementation of the method according to the invention is insensitive to spatial variations of the illumination and to the Fixed-Pattern-Noise. Furthermore, it is possible to accurately characterize and classify the particles manipulated in the device without the need of pumps or liquid flows otherwise generated, which cause a not well determined positioning of the analyzed particles.

Finally, contrary to the approaches which make use of flows for moving the particles, by using a controlled force field for moving the particles relative to the sensor, a greater quantity of information is obtained, consisting for example of the movement speed of the particle in response to the force field. Therefore, an additional information source on the characteristics of the particle is obtained. This information can be advantageously used for differentiating the different types of particles.

Further features and advantages of the invention will be apparent from the following description of some non limiting embodiments of the same, which is carried out with reference to the figures of the attached drawings.

DETAILED DESCRIPTION

The aim of the present invention is to provide a method and an apparatus for carrying out the manipulation and/or the detection of particles.

Figure 1:
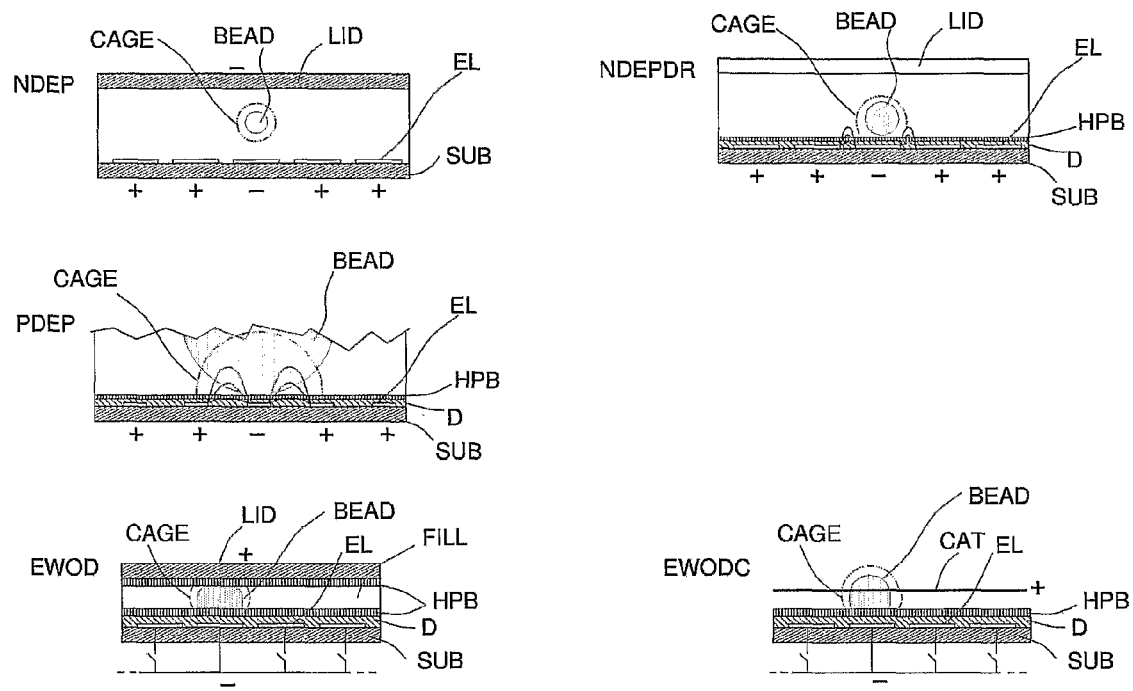
FIG. 1 shows the principle of generation of force fields through arrays of electrodes.

The method of the invention is based on the use of a non uniform force field (F) through which single particles or groups of particles (BEADS) are attracted towards positions of stable equilibrium (CAGE) (FIG. 1). Such field can be for example a negative (NDEP) or a positive (PDEP) dielectrophoresis field (DEP), an electrophoretic field (EF) or an electro-hydrodynamic (EHD) motions field or still electro-wetting on dielectric (EWOD).

The detection can concern one of the following aspects, or combinations of the same:
1. the counting of single particles or the quantification;
2. the identification and/or characterization;
3. the localization.

Concerning this, the measurement of the impedance variation and/or the measurement of the luminous intensity variation transmitted, diffused or emitted in fluorescence is mainly exploited.

Generation of the Forces

There are different methods for the generation of forces for moving particles, according to the known art (FIG. 1), through arrays of electrodes (EL), provided on a substrate. Typically, a cover (LID) is used, which can be in turn an electrode, which delimits a micro-chamber within which the particles (BEADS) are typically found in a liquid suspension. Some diagrams for the different forces are reported in FIG. 1. In case of dielectrophoresis (DEP), the voltages applied are in phase periodic voltages (Vphip) shown with the addition symbol (+) and counter-phase periodic voltages (Vphin) shown with the subtraction symbol (−). By counter-phase voltages, voltages out of phase of 180 degrees are meant. The field generates a force which acts on the particles, attracted towards points of equilibrium (CAGE).

In case of negative DEP (NDEP), it is possible to generate closed force cages, according to the known art, if the cover (LID) is a conductive electrode; in this case, the point of equilibrium (CAGE) is provided in correspondence with each electrode connected with Vphin(−) if the adjacent electrodes are connected with the opposite phase Vphip (+) and if the cover (LID) is connected with the phase Vphin (−). Such point of equilibrium (CAGE) is normally spaced apart in the liquid relative to the electrodes, whereby the particles (BEAD) are, in a steady state, in levitation. In case of positive DEP (PDEP), the point of equilibrium (CAGE) is normally found in correspondence with the surface on which the electrodes are provided, and the particles (BEADS) are, in a steady state, contacting with the same. For the PDEP, the presence of further electrodes in the cover is not necessary, because the points of equilibrium of the PDEP correspond to the maxima of the electric field. An array of electrodes can be used for electrophoresis, in order to attract charged particles towards the electrodes with an opposite polarity. For the electro-hydrodynamic (EHD) motions, the configurations of the electrodes generate some flows which drive the particles towards points of minimum flow. For the EWOD, a cover (LID) containing a dielectric-coated electrode is generally used, and the matrix of electrodes is energized by counter-phase signals with respect to the cover in the points in which the particles (typically liquid droplets in air) have to be attracted. The electrodes on which the particle must not be present, on the contrary, are left floating. For the EWOD, by manipulating droplets in air, above the array of electrodes, a series of wires can be used alternatively to the cover.

In the following, for easiness, the use of closed negative dielectrophoresis cages as an execution force for the description of the methods and apparatus of the invention is merely considered by way of non limiting example for the purposes of the present invention (for this reason, a lid acting as an electrode has to be used). To those skilled in the art with ordinary abilities, it is apparent how to generalize the methods and the apparatus described below for the use of different execution forces and different types of particles.

Sensors Employed

Always for simplicity, in the following reference will be only made to the case of the optical sensors, which allow to detect the incident optical power on a photodiode integrated with the electrodes. To those skilled in the art with ordinary abilities, it is apparent how to generalize, in the different cases, the methods and apparatus described below also for the alternative or combined use of integrated impedance meter sensors.

In the following, for simplicity, the term "grey level" will also be used as a synonymous of "exiting signal from the integrated sensor". This signal, in turn, could be proportional to the "incident optical power" (on an optical sensor, such as a photodiode) or to the measured impedance (in case of integrated impedance meter sensors).

Methods for the Use of the Optical Sensors

In case of optical sensors, reference will be generally made to the case of bright-field (or BF)-type illumination. In this case, the illumination strikes on the sensor. Dark-field (or DF) illumination methods, or based on fluorescence are also possible and fall within the object of the present invention, but for easiness they will not be listed for all the methods treated below, but are only discussed herein.

Figure 17:
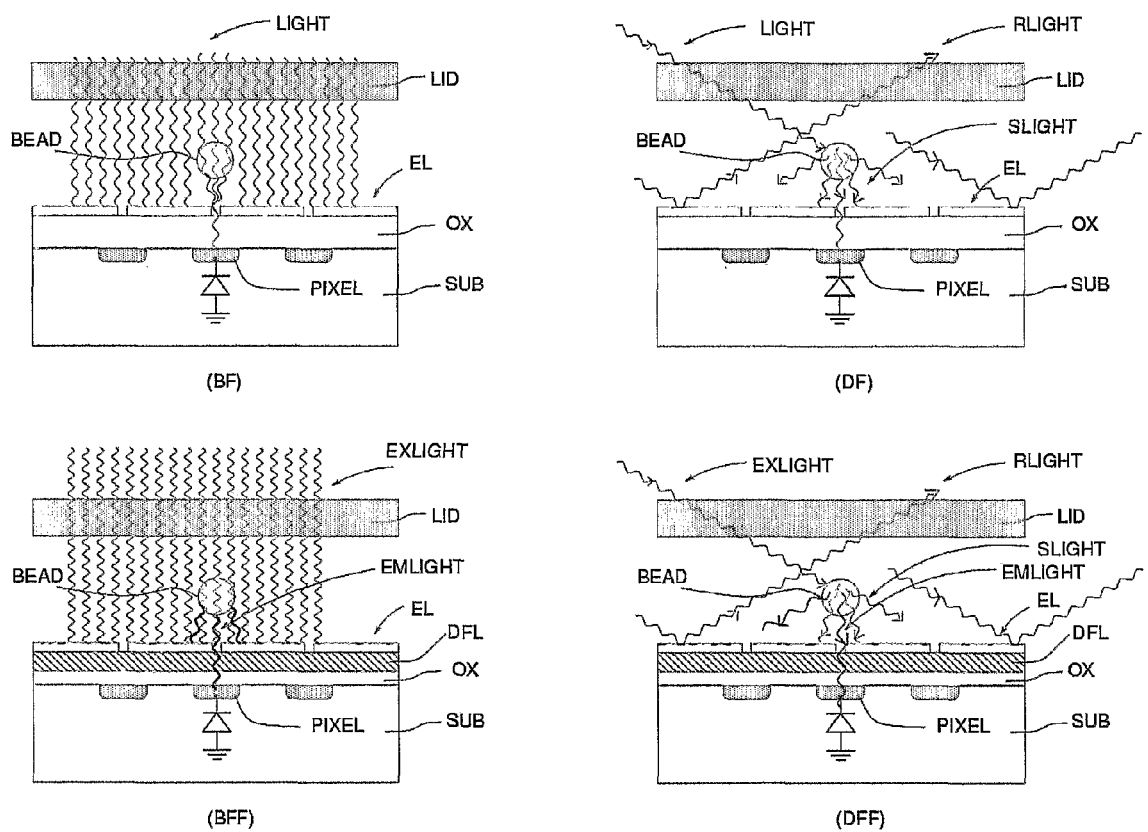
FIG. 17 shows some different illumination and optical detection modes.

In FIG. 17, some methods for the use of the optical sensors are shown. The figure relates to the section of a device with optical sensors (PIXEL) integrated in a substrate (SUB). The dielectric between the sensors and the different metallizing layers which provide the electrodes (EL), can simply consist of an oxide (OX) layer or also include a filter layer (DFL), for example realized with the thin-film dichroic mirrors technology.

In the diagram of bright-field detection (FIG. 17-BF), the lighting (LIGHT) comes from the cover (LID) and the optical power detected by the sensors is substantially varying as a function of the distortion and the absorption caused by the particle (BEAD).

In the diagram of dark-field detection (FIG. 17-DF), the lighting (LIGHT) comes through the cover (LID) at such an angle of incidence that it does not directly reach the sensors (PIXEL), and the optical power detected by the sensors is substantially varying as a function of the diffuse radiation (SLIGHT) from the particle (BEAD) hit by the lighting in a direct way (LIGHT), or, in case, following to a reflection on the electrodes (RLIGHT).

In the diagram of bright-field fluorescence detection (FIG. 17-BFF), the excitation (EXLIGHT) comes from the cover (LID) and the optical power detected by the sensors is substantially varying as a function of the emitted fluorescence (EMLIGHT) by the particle (BEAD). In this case, in order that the emitted light (EMLIGHT) signal is not overcome by the excitation power (EXLIGHT), it is advisable to use one or more of the following tricks:

use a filter layer (DFL) for the wavelength of the radiation emitted for the excitation;
use an excitation frequency for which the optical sensor (PIXEL) has a low quantum efficiency (i.e. it is relatively insensitive to that wavelength). This is possible, for example, by using p-n joints at a relatively high depth, and an excitation radiation with a wavelength preferably in the UV, in particular better if lower than 380 nm.

In the diagram of the dark-field fluorescence detection (FIG. 17-DFF), the excitation (EXLIGHT) comes from the cover (LID) at such an angle of incidence that it does not directly reach the sensors (PIXEL), and the optical power detected by the sensors is substantially varying as a function of the fluorescence emitted from the particle (BEAD) hit by the light in a direct way (EXLIGHT), or, in case, following to a reflection on the electrodes (RLIGHT). In order that the emitted light (EMLIGHT) signal is not degraded by the power of the light diffused by the particle (SLIGHT), it is however desirable to use one or more of the triks above mentioned in case of bright-field fluorescence, so as to improve the selectivity of the system.

Figure 12:
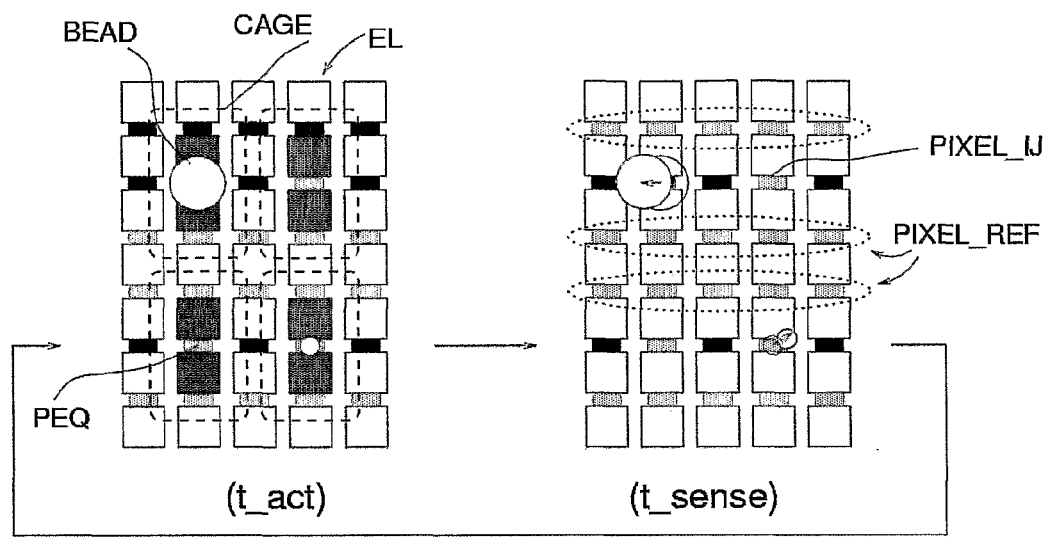
FIG. 12 shows an elemental sequence of steps shown for the simultaneous detection of all the particles without the need of moving the cages.

Method for the Detection of the Full Cages Through Activation and Deactivation of the Cages FIG. 12 shows a possible sequence of steps of the method according to the present invention, in order to detect which cages are full (at least a particle is enclosed) and which are empty, without the need of displacing the cages themselves.

This method is particularly suitable when the pattern applied to the electrodes is so thick not to allow the cages to be displaced. Furthermore, it can be advantageous if in the device, circuits for the displacement of the cages are not present.

The method is based on the alternation of execution phases, for the entrapment/release of the particles (BEAD) in the cages (CAGE) and sensing, during which one or more images are acquired by the integrated sensors (PIXEL).

Figure 13:
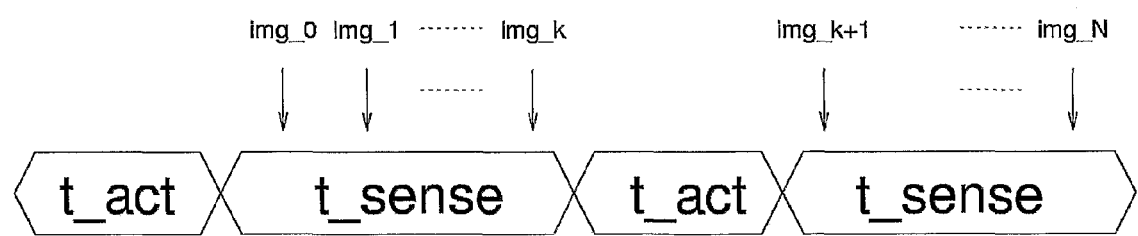
FIG. 13 shows the wave forms relating to the detection and characterization method based on the activation and the deactivation of cages of FIG. 12.

The wave forms are schematized in FIG. 13.

On the deactivation of the cages, the particles start to deposit by settling, and/or to laterally displace themselves (right part of FIG. 12—t_sense) due to the Brownian movements, starting from the position of stable equilibrium (PEQ) which they assume when caged. Because of these displacements, the grey levels detected in full cages vary in a substantially higher way with respect to the variations of the grey levels associated with the thermal noise of the reading circuit and/or the light system, which occur on the sensors (pixel) relating to empty cages.

The classification of empty or full cage takes place as follows:

1. A series of images is acquired (sensing) by alternating operation (activation or deactivation) of the cages (for times in the order of some seconds to some fraction of a second) and sensing of one or more images (for times in the order of a fraction of a second, e.g. 100 ms, to tens of seconds).

2. For a series of images NIMG, for each sensor PIXEL_IJ associated with a CAGE_IJ, the non-normalized standard deviation of the grey level is calculated (in this particular case proportional to the incident optical power) on the sensor, defined as $$\tilde{\sigma}_{ij\text{-}NIMG} = \sqrt{\sum_{k=1}^{NIMG} (PIXEL\_IJ_k - M\_IJ_{NIMG})^2}$$

with $$M\_IJ_{NIMG} = \frac{1}{NIMG} \sum_{k=1}^{NIMG} PIXEL\_IJ_k$$

(average value of the grey level of PIXEL_IJ in the series of images NIMG).

3. The non-normalized standard deviation average of the grey level on empty reference sensors (PIXEL_REF), and the relative standard deviation of the non-normalized $$M_{REF\text{-}NIMG} = \frac{1}{NREF} \sum_{r=1}^{NREF} \tilde{\sigma}_{r\text{-}NIMG}$$

standard deviation $$\sigma_{REF\text{-}NIMG} = \sqrt{\frac{1}{NREF} \sum_{r=1}^{NREF} (\tilde{\sigma}_{r\text{-}NIMG} - M_{REF\text{-}NIMG})^2}$$

are calculated

4. A classification threshold is defined.

$THR = M_{REF\text{-}NIMG} + \alpha \cdot \sigma_{REF\text{-}NIMG} + \Delta$. Typical values are $\alpha=1, \Delta=0$.

5. The cages IJ are classified as full, whereby $\tilde{\sigma}_{ij\text{-}NIMG} >$ THR and the remaining cages are classified as empty, whereby It is interesting to $\tilde{\sigma}_{ij\text{-}NIMG} \leq$ THR. note that such method is independent from the Fixed-Pattern-Noise (fixed spatial noise bound to the dispersion of the characteristics of the photodiodes), as it considers the signal power with respect to the average value per sensor, but leaves out the absolute value of such average value.

It is typically sufficient to carry out a number of measurements (that is to acquire a number of images) NIMG=50-100 in order to obtain an accuracy higher than 95%.

A dynamic measurement of the number of images NIMG which has to be acquired can be obtained considering the number of images required for converging the standard deviation (normalized) of the reference pixels $$\sigma_{r\text{-}NIMG} = \sqrt{\frac{1}{NIMG} \sum_{k=1}^{NIMG} (PIXEL\_r_k - M\_r_{NIMG})^2}$$

to its asymptotic value.

This asymptotic value is constant if the noise 1/f bound to the light variations is negligible (wherein f is the general frequency in which the noise is considered).

Therefore, in more general terms, the method just described with a specific reference to the case of using optical sensors allows to carry out the detection of the presence of particles (BEADS), if any, existing in points of stable equilibrium (PEQ) of any force field (F) (therefore not only a dielectrophoretic one) acting on the particles (for example cells) and generated by an array of electrodes (EL). Such method includes the steps of:

i. deactivating the force field (F);

ii. measuring, in at least a time interval following to the deactivation and selected as a function of the dynamic of the settling and/or Brownian movements to which the particles with a deactivated field are subjected, the grey level generated by first sensors (PIXEL_IJ) associated with points of stable equilibrium (PEQ) and by second sensors (PIXEL_REF) associated with space regions which certainly can not be occupied by particles because of the current configuration of the force field (F);

iii. reactivating the force field (F);

iv. repeating the steps from i) to iii) a number of times, substantially comparable with the convergence rate to its asymptotic value, of the variance of the grey level values measured on the second sensors, assumed as a reference (PIXEL_REF);

v. classifying a point of equilibrium as occupied by particles if, in the considered temporal series of measurements, the standard deviation of the grey level values detected on the first sensors, associated with such point of equilibrium (PEQ), results higher than a pre-fixed threshold (THR).

Method for the Detection of the Full Cages by Movement of Cages and Measurement of the Difference of the Static Value of the Grey Levels.

Figure 10:
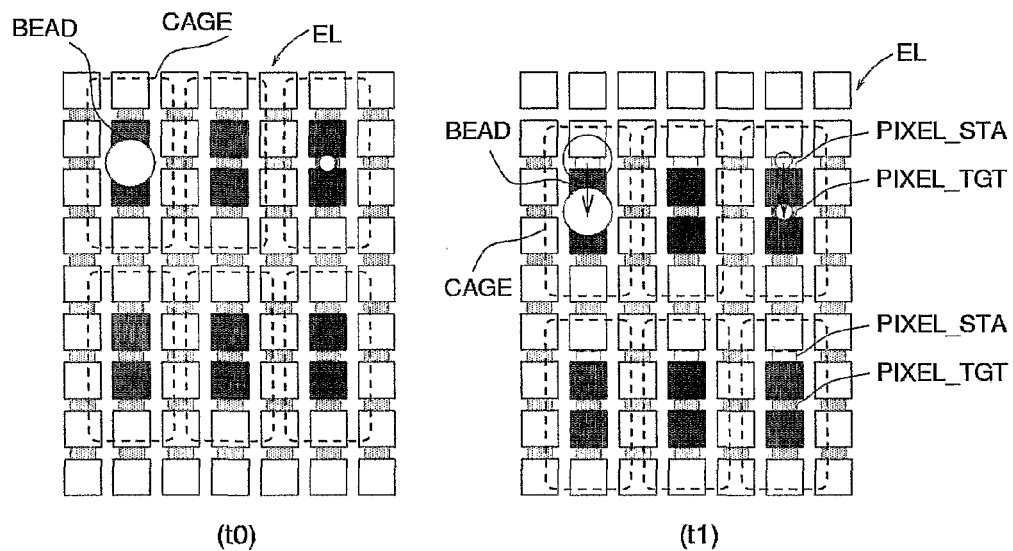
FIG. 10 shows an elemental sequence of steps useful for the simultaneous detection of all the particles through the movement of all the cages.

FIG. 10 shows the steps of a sequence of operations according to the present method for detecting the full cages through a movement of the same and an analysis of the static values of the grey levels.

1. In a first instant (t0) the cages (CAGE) place the particles (BEADS) on respective sets of initial optical sensors (PIXEL_STA). An image with the grey levels corresponding with this configuration is acquired.

2. At the following time (t1), once the transient bound to the cages movement is exhausted, the particles arrange themselves in correspondence with final optical sensors (PIXEL_TGT). A new image with the grey levels corresponding with this configuration is acquired.

3. The difference image of the grey levels in relation to images of the points 1 and 2 is determined.

4. The absolute value of the difference image is determined.

5. The grey level resulting for the pairs of pixels (PIXEL_STA, PIXEL_TGT) relating to the starting and final positions of each cage is determined.

6. The steps from 1 to 4 are repeated NDIFF times and the grey levels for each cage relating to the absolute variation determined at the step 5 are accumulated.

7. Analogously to what above described for the classification with activation/deactivation of the cages, a classification threshold THR is determined, considering, this time, average and standard deviation of the absolute value of the differences corresponding with certainly empty sensors (pixels) (such as, for example, the pixels between rows of cages), for all the difference images NDIFF acquired.

In more general terms, the detection of the presence of particles (BEADS) existing, if any, in points of stable equilibrium (PEQ) of a force field (F) acting on the particles, generated by an array of electrodes (EL) takes place by
i) first measuring the grey level generated by first sensors (PIXEL_STA) associated with stable points of equilibrium (PEQ), and by reference sensors (PIXEL_REF) associated with space regions which certainly can not be occupied by particles in this first current configuration of the force field (F);
ii) next, modifying the force field (F) in order to impart it a second current configuration wherein the points of stable equilibrium are displaced in correspondence with second sensors (PIXEL_TGT), different from the first sensors;
iii) next, measuring the grey level generated by the second sensors (PIXEL_TGT) and reference sensors (PIXEL_REF) associated with space regions which can not certainly be occupied by particles in the second current configuration of the force field (F);
iv) determining the difference (DIFF_IMG) between the grey level values detected to the preceding points;
v) repeating the steps i) to iv);
vi) processing differential grey level values in order to classify the points of stable equilibrium (PEQ) occupied by particles and those not occupied.

Such processing includes the steps of vii) determining the absolute value of the differences in grey levels, and then viii) classifying as occupied the points of equilibrium associated with sensors for which a variation substantially higher than the average variation of the grey level associated with reference sensors which can not be occupied by particles in the first and second configurations of the field (F) is detected.

This method, based on the absolute value of image differences, is also immune from the Fixed-Pattern-Noise and, likewise to the method with activation/deactivation of the cages, is rather insensitive to unevenness in the illumination.

With respect to the first method, it has the disadvantage of requiring circuits for the displacement of the cages and a distance between the same which allows such a movement thereof to determine in an univocal way the displacement of the caged cell, if any.

One of the advantages of this method is that a few images (and reduced times) are typically required in order to obtain a certain classification quality (low chances of error) which, with the method of activation/deactivation of the cages, requires more images and more time.

Figure 11:
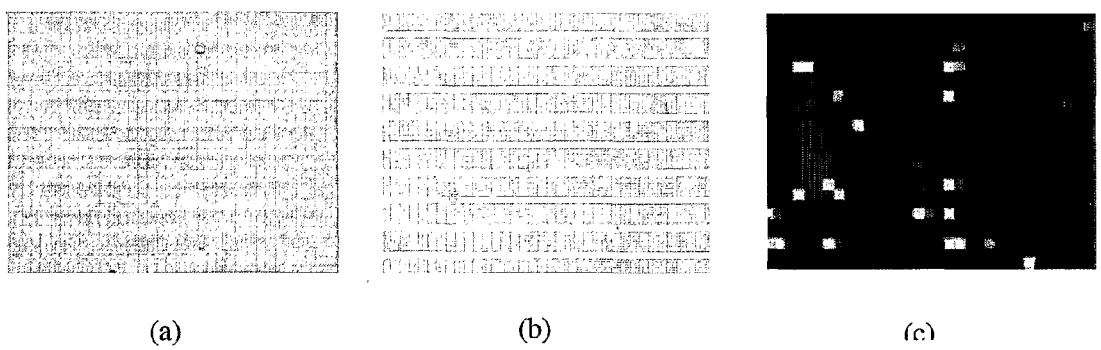
FIG. 11 shows three images which can be acquired through the implementation of the sequence of steps of FIG. 10.

In FIG. 11, the result which can be obtained with a single step (NDIFF=1) is shown. In FIG. 11 (a), the image detectable by the optical microscope is reported, in FIG. 11 (b) the map of the corresponding grey values is shown (with a compensation of the Fixed-Pattern-Noise) and on the contrary, in FIG. 11 (c) the normalized image of the absolute value of the difference between the image with initial grey values and after a displacement rightward is shown.

Method for the Detection of the Full Cages Through Movement of Cages and Measurement of the Dynamic Value of the Grey Levels.

Figure 2:
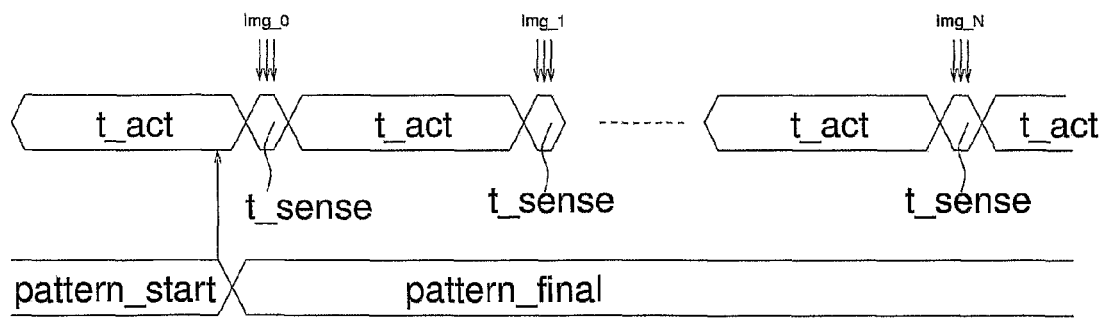
FIG. 2 shows the wave forms relating to the method of detection and characterization based on a displacement of cages of FIGS. 4 and 9.

FIG. 2 shows the wave forms in the steps of the methods for the dynamic detection of the presence of particles in the cages through displacement of the cages themselves.

At the beginning, a displacement of the cages is carried out but without waiting the settling of the particles in their new position of equilibrium and the signal variations of the optical sensors above which the cells (particles) contained in the moving cages are moving, are detected.

Figure 4:
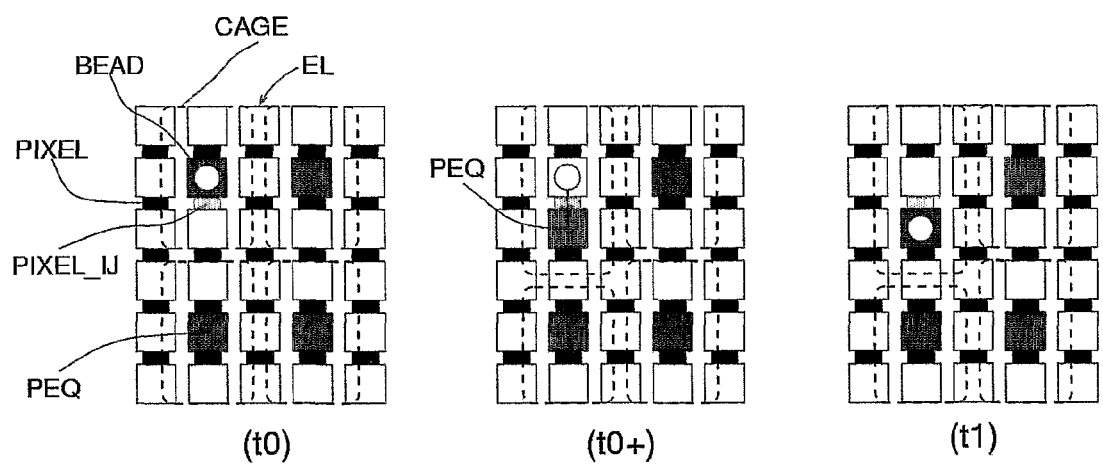
FIG. 4 shows a sequence of steps for the detection/characterization of particles with dimensions lower than the electrode.

FIG. 4 shows a sequence of steps which involves the movement of the cage in the IJ position and the displacement of the point of equilibrium (PEQ) which determines the passage on the particle (BEAD) on the optical sensor (PIXEL_IJ).

Figure 9:
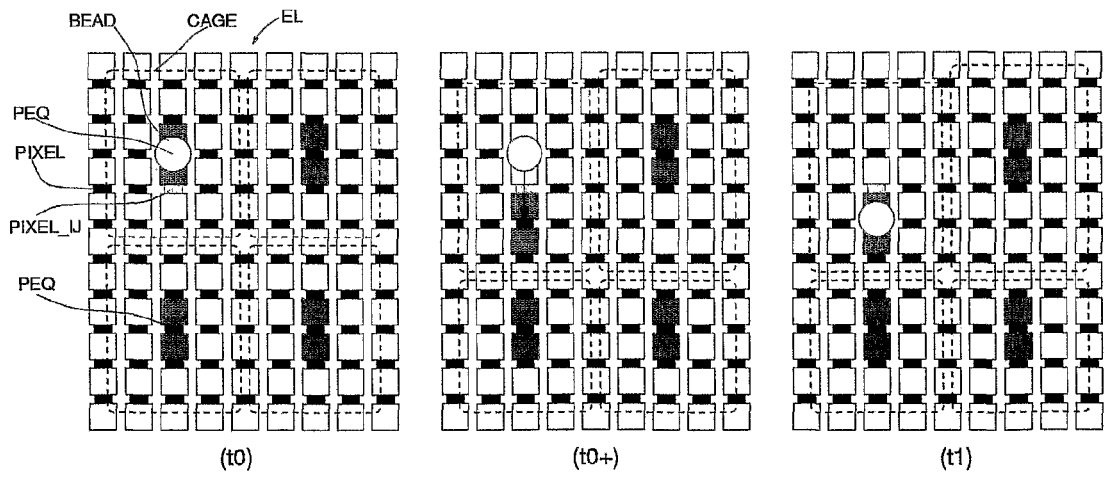
FIG. 9 shows a sequence of steps useful for the detection/characterization of particles with dimensions higher than an electrode, but lower than two electrodes.

If the dimensions of the particle (BEAD) are higher than those of the electrode, the sensor will measure a variation but it does not reach the base value relating to the pixel without particles above it. In this case, a diagram slightly different can be adopted, as in FIG. 9. This case, by measuring the grey value on the pixel (PIXEL_IJ) on the edge of a cage with higher dimensions than an electrode, reproduces a situation corresponding to that of having electrodes with double dimensions than the actual dimensions of the electrode.

This technique allows, in one sense, to scan the cell by detecting the grey values associated with the incident power considering the integral with respect to horizontal sections of the same (if the photodiode is as large as the cell and this is vertically moved). By changing the duty-cycle of the execution, a different scanning rate is obtained.

$$\frac{t_{act}}{(t_{act} + t_{sense})}$$

These operations allow to detect the presence of particles based on the luminosity peaks and valleys which occur when the cage is full. By processing the signals of the sensors, a person skilled in the art can easily detect a series of parameters (for example the peak-peak amplitude of the grey value) which allow to discriminate full cages from empty cages.

Therefore, according to this variant of the method of the invention, the presence of existing particles (BEAD), if any, in points of stable equilibrium (PEQ) of a force field (F) acting on the particles, generated by an array of electrodes (EL) is detected by carrying out the following steps:
i. modify the force field (F) so as to move the points of stable equilibrium (PEQ) by passing the particles (BEADS) in correspondence with respective sensors (PIXEL_IJ);
ii. measuring the grey level generated by sensors (PIXEL IJ) associated with the passage of the different points of stable equilibrium (PEQ) with a substantially higher frequency than the settling time of the particles in the new position of equilibrium;
iii. classify the presence or the absence of particles through the measurement of characteristic parameters of the temporal evolution of the measurement of the grey level generated by the sensors, for example based on the incident optical power, in case of optical sensors.

The measurement of the grey level generated by the sensors, namely the optical power striking on the same, can obviously take place also alternating the steps of activation of the field acting on the particle; and deactivation of the aforesaid field, in order to measure, afterwards, the incident optical power, that is the grey level thus obtained; this is advantageous for avoiding any interference between the execution voltages with the reading of the sensors, even if in principle it is not necessary if there is a substantial independence of the sensors from the activation of the execution voltages.

The parameters of the temporal evolution of the measurement of the optical power preferably include the peak to peak amplitude of the grey level, and preferably the classification takes place through the comparison with a threshold value determined starting from peak to peak measurements of the optical power, namely the grey level, on reference sensors which can not be occupied by particles with the configuration of the considered force field (F), increased by a factor proportional to the standard deviation of the peak to peak values of the reference sensors.

In this way, also the compensation of the noise 1/f due to the environment illumination existing on the reference sensors is obtained.

Method for the Counting of Cells Based on the Number of Full Cages, with Error Compensation By the methods above described, the number of full cages is then determined. The aim of the present invention is also to find out a method for the counting of the cells in the cages. From this, the volume of the considered sample being known, also the concentration of the cells is obtained.

As a first approximation, especially if the average number of cells per cage is substantially lower than about 0.1, the number of full cages is approximately similar to the number of cells (in this case there is an underevaluation of the number of cells of about 5%). For a higher average number of cells, according to the present invention, the distribution statistics of the cells per cages can be compensated, in order to obtain a counting which approximates with a greater precision to the actual number of cells on the chip.

We assume that the following suppositions occur:

1. The cells are uniformly distributed per volume unit; this hypothesis is overall verified in the cases in which the sample is injected in the empty micro-chamber.

If, on the contrary, the sample is injected in the microchamber previously filled of buffer, the sample could be only locally uniform, because of the variations of cells density bound to the flow profile of the sample.

2. The bonds connected with the maximum number of cells per cage can be ignored.

This hypothesis is verified when the total volume of the cells (average volume of a cell per average number of cells) is reasonably lower than the volume of a cage (intended as the volume of the basin of attraction of each cage).

Under these hypothesis, the statistical distribution of the cells is represented by the binomial distribution. We define:
NCAGES=number of cages in the chip (or considered portion)
n=NCELLS=number of cells in the chip (or considered portion)
wherein by "chip" the set formed by the array of electrodes EL is intended, which is precisely normally integrated in a single multilayer chip together with the sensors PIXEL.
Then, the probability that a cell belongs to the basin of attraction of any cage is:

$$p = 1/NCAGES$$

The probability of having k cells per cage results from the formula:

$$P[k] = \binom{n}{k} \cdot p^k \cdot (1-p)^{n-k}$$

$$\text{wherein is } \binom{n}{k} = \frac{n!}{k!(n-k)!}$$

the number of combinations of n objects taken k at a time (binomial distribution).

The average value of cells per cage (Average Cells Per Cage—ACPC) is $$ACPC = <P[k]> = p \cdot n = \frac{NCELLS}{NCAGES}$$

As on the chip there are typically many cages, the probability of having 1, 2, . . . k cells per cage, multiplied by the number of cages, approximates well the actual value of cages with 1, 2, . . . k cells. Considering this, and the total number of empty and full cages being detected, the average value of cells per cage (ACPC) can be estimated, by calculating the value which provides an expected number of full and empty cages corresponding with the detected value.

The expected value of empty cages is calculated as $$\begin{aligned} EC_{estimate} &= NCAGES \cdot P[0] \\ &= NCAGES \cdot (1-p)^n \\ &= NCAGES \cdot \left(1 - \frac{1}{NCAGES}\right)^{NCELLS} \end{aligned}$$

and by replacing the value of the empty cages actually detected, the counting of cells is then obtained, which can be calculated with simple passages such as $$NCELLS_{measure} = \frac{\log(NCAGES) - \log(EC_{measure})}{\log(NCAGES) - \log(NCAGES - 1)}$$

A better estimation of the number of cells is thus obtained, and the precision of the counting results good also for ACPC values higher than one, provided that the number of empty and full cages is statistically significant; in this way, in fact, the error bound to the underevaluation of the number of cells otherwise associated with the counting of the full cages alone is mitigated. Obviously, the detected number of empty cages ($EC_{measure}$) must be greater than zero and results lower or equal to the number of cages NCAGES. The following table numerically shows the case for a particular example with 6400 cages, and different concentrations of cells. As it can be noted, the counting error is drastically reduced, especially for high average concentrations of cells per cage. Actually, the reported value is simply the one based on the density of probabilities, but given the great number of cages, the probability estimation approximates well a possible measured value.

TABLE 1

| NCAGES | | 6400 | | | 6400 | | | 6400 | | | 6400 | |
|---|---|---|---|---|---|---|---|---|---|---|---|---|
| NCELLS | | 640 | | | 3200 | | | 6400 | | | 12800 | |
| ACPC | | 0.100 | | | 0.500 | | | 1.000 | | | 2.000 | |
| k | P[k] | cages | cells | P[k] | cages | cells | P[k] | Cages | cells | P[k] | cages | cells |
| 0 | 90.48% | 5791 | 0 | 60.65% | 3882 | 0 | 36.79% | 2354 | 0 | 13.53% | 866 | 0 |
| 1 | 9.05% | 579 | 579 | 30.33% | 1941 | 1941 | 36.79% | 2355 | 2355 | 27.07% | 1732 | 1732 |
| 2 | 0.45% | 29 | 58 | 7.58% | 485 | 970 | 18.40% | 1177 | 2354 | 27.07% | 1732 | 3464 |
| 3 | 0.02% | 1 | 3 | 1.26% | 81 | 243 | 6.13% | 392 | 1176 | 18.05% | 1155 | 3465 |
| 4 | 0.00% | 0 | 0 | 0.16% | 10 | 40 | 1.53% | 98 | 392 | 9.02% | 577 | 2308 |
| 5 | 0.00% | 0 | 0 | 0.02% | 1 | 5 | 0.31% | 20 | 100 | 3.61% | 231 | 1155 |
| 6 | 0.00% | 0 | 0 | 0.00% | 0 | 0 | 0.05% | 3 | 18 | 1.20% | 77 | 462 |
| 7 | 0.00% | 0 | 0 | 0.00% | 0 | 0 | 0.01% | 0 | 0 | 0.34% | 22 | 154 |
| 8 | 0.00% | 0 | 0 | 0.00% | 0 | 0 | 0.00% | 0 | 0 | 0.09% | 5 | 40 |
| 9 | 0.00% | 0 | 0 | 0.00% | 0 | 0 | 0.00% | 0 | 0 | 0.02% | 1 | 9 |
| 10 | 0.00% | 0 | 0 | 0.00% | 0 | 0 | 0.00% | 0 | 0 | 0.00% | 0 | 0 |
| 11 | 0.00% | 0 | 0 | 0.00% | 0 | 0 | 0.00% | 0 | 0 | 0.00% | 0 | 0 |
| 12 | 0.00% | 0 | 0 | 0.00% | 0 | 0 | 0.00% | 0 | 0 | 0.00% | 0 | 0 |
| 13 | 0.00% | 0 | 0 | 0.00% | 0 | 0 | 0.00% | 0 | 0 | 0.00% | 0 | 0 |
| 14 | 0.00% | 0 | 0 | 0.00% | 0 | 0 | 0.00% | 0 | 0 | 0.00% | 0 | 0 |
| 15 | 0.00% | 0 | 0 | 0.00% | 0 | 0 | 0.00% | 0 | 0 | 0.00% | 0 | 0 |
| total | | 609 | 640 | | 2518 | 3199 | | 4045 | 6395 | | 5532 | 12789 |
| counting error | | −4.84% | 0.00% | | −21.31% | −0.03% | | −36.80% | −0.08% | | −56.78% | −0.09% |

In other words, according to this method, from the counting of full and empty cages, carried out according to any one of the method described so far, the counting of the total number of particles (for example cells) actually existing in a sample injected in a chamber defined by the array of electrodes EL and the cover (LID), if any, can be derived; the counting step of the single particles, of which the general presence has been previously detected, takes place according to this aspect of the invention in an estimated way on statistical bases, as follows:

a) the number ($EC_{measure}$) of points of stable equilibrium (PEQ) existing in the field (F) generated by the array of electrodes (EL)—points of stable equilibrium, hereinbelow also shown as—cages—which do not contain any particle (BEAD) is measured by the sensors.

b) The counting (NCELLS) of particles (BEAD) is determined as the ratio of the difference between the logarithm of the number (NCAGES) of points of stable equilibrium (PEQ) to the logarithm of the measured number ($EC_{measure}$) of the points of stable equilibrium (PEQ) non containing any particle, and the difference between the logarithm of the number (NCAGES) of points of stable equilibrium (PEQ) and the logarithm of the number (NCAGES−1) of the points of stable equilibrium (PEQ) less one.

Method of Characterization of the Cells in the Cages Through Movement of the Cages and Measurement of the Dynamic Value of the Grey Levels.

Figure 3:
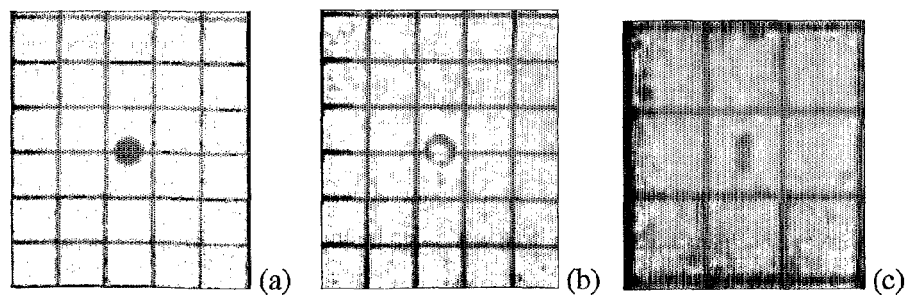
FIG. 3 shows microscopically images of (a) a polystyrene ball, (b) a K 562 cell, (c) a red cell.

As it is shown in FIG. 3, since a ball (ex. FIG. 3 (a)), a cell of a type (ex. a K562, as in FIG. 3 (b)), or a cell of another type (ex. a red cell as in FIG. 3 (c)), have different dimensions, shape, absorbance profile and index of refraction, by passing the cage on a sensor it is possible to detect not only if it is full but also, according to a further aspect of the present invention, to characterize the type of the existing particle, if any.

A cell (and certain types of micro-balls) show a light distortion (a kind of a lens effect) which causes a variation of the grey level with negative peaks (dark edges on the cell) and positive peaks (brighter centre where the cell concentrates the light) of the grey level.

Figure 5:
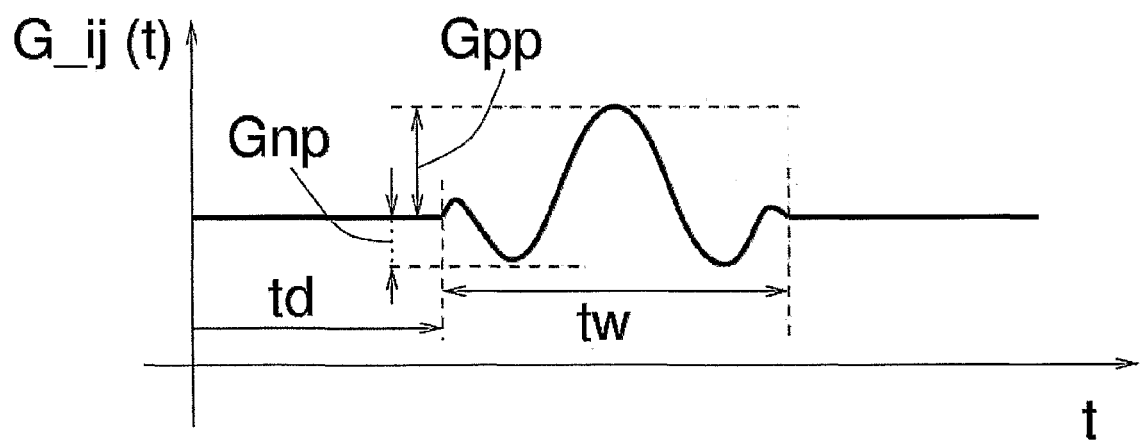
FIG. 5 shows a diagram of a typical temporal course of the grey value detected at the passage of a cell or balls with dimensions in the order of 15-20 μm, and the indication of some possible discriminant parameters.

Parameters bound to the dynamic evolution of the grey level, such as, by a significant but not limiting example reported in FIG. 5, the measurement of the amplitude of the negative (Gnp) and positive (Gpp) peaks of the grey level, as well as for example the delay (td) between cage movement and detection of the first grey variation, or also the temporal length of the variations can be used for obtaining additional information and classifying the kind of cell.

Formulas:

The displacement speed is, as a first approximation, proportional to the dielectrophoretic mobility, and results $v \propto k \cdot R^2$. The length of the variation of the grey levels, as a first approximation, therefore results, namely inversely proportional to the radius of the particle (it decreases when R increases). The time delay td between $$t_w = \frac{2R}{kR^2} \propto \frac{1}{R},$$

execution and start of the variation of the grey level results as a first approximation (in the case of FIG. 4, with a cell on a single electrode) equal to
(it also decreases when R increases).

Figure 6:
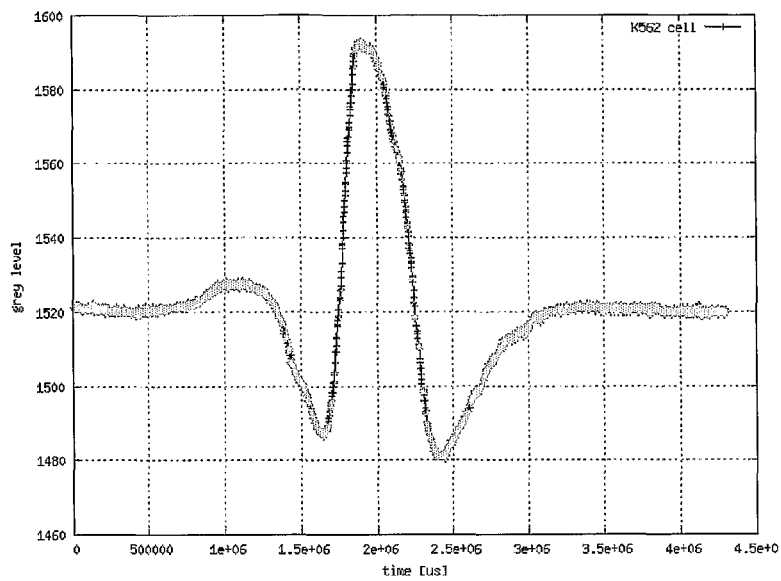
FIG. 6 shows the temporal evolution of the grey value detected at the passage of a K562 cell following to the displacement of its cage.

FIG. 6 shows the actual course measured for a K562 cell.

$$t_d = \frac{W_{EL} - R}{kR^2}$$

Figure 7:
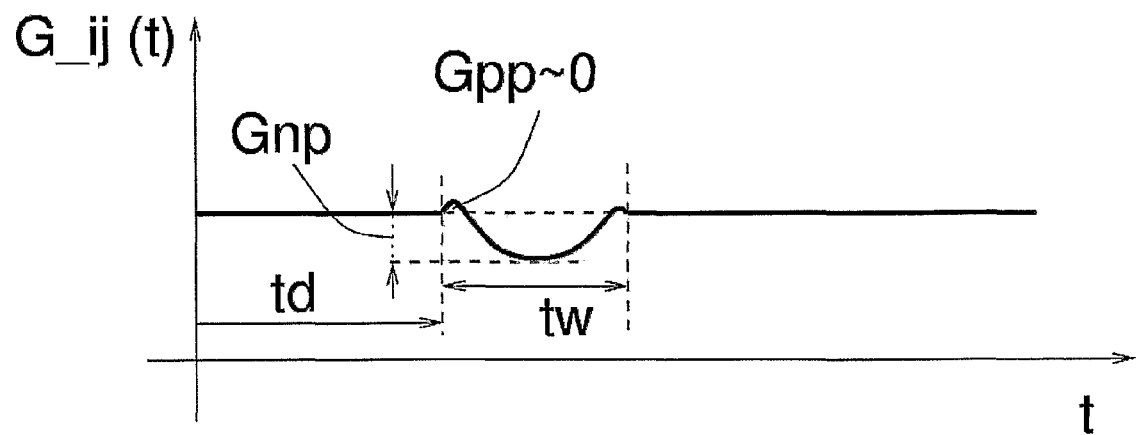
FIG. 7 shows a diagram of a typical temporal course of the grey value detected at the passage of a small cell or microball, and the indication of some possible discriminant parameters.

FIG. 7 shows the typical course expected for non transparent balls, or small cells for which the effect of the absorbance compared to the above mentioned "lens" effect is predominant.

Figure 8:
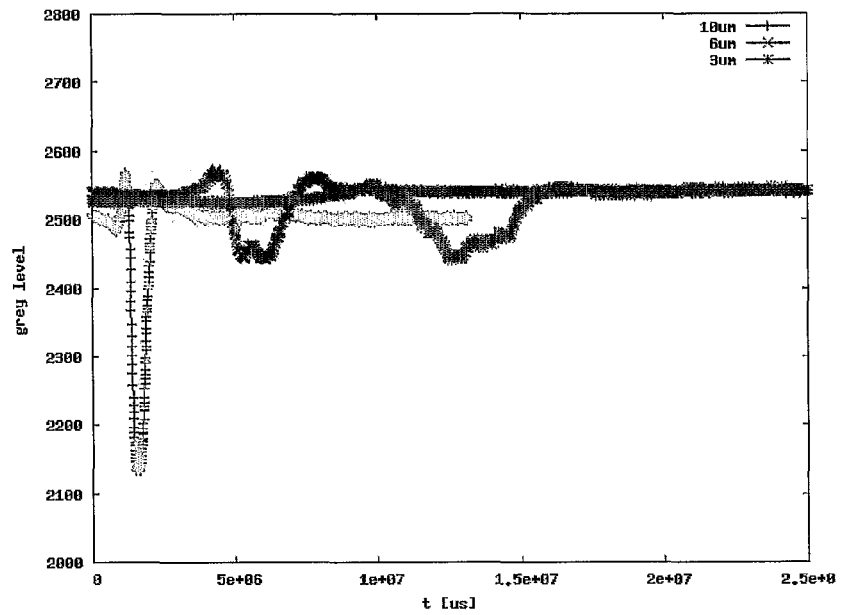
FIG. 8 shows the temporal evolution of the grey value detected at the passage of a polystyrene ball of 10 μm, 6 μm and 3 μm, respectively, following to the displacement of its cage.

FIG. 8 shows the temporal evolution of the grey value detected at the passage of polystyrene balls with 10 μm, 6 μm and 3 μm following to the displacement of its cage.

By extracting opportune discriminating parameters, it is possible, in an apparent way for those skilled in the art, to define a classification criterion, similarly to what above mentioned for the classification of full and empty cages.

In particular, the identification method can include the extraction of the discriminating characteristics of the particles, and the use of algorithms based on neural networks, first close ks, thresholds algorithms and/or Principal Component Analysis, or a combination of the same.

Figure 14:
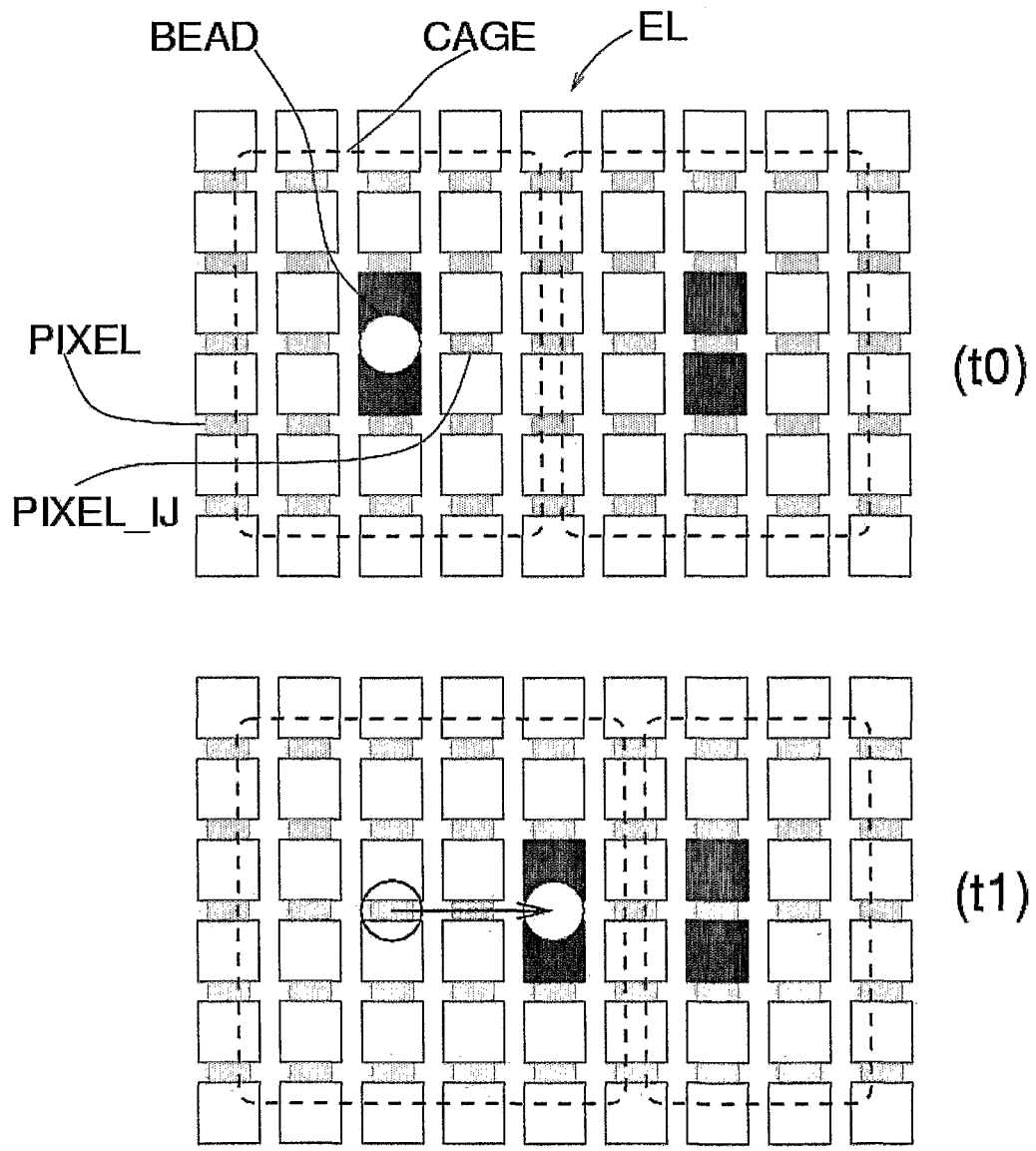
FIG. 14 shows another sequence of steps useful for the detection/characterization of particles in a cage.

FIG. 14 shows an alternative technique based on the same principle, through which it is possible to scan the cell with a greater resolution in its horizontal section, by laterally moving it above the sensor. In fact, the "slice" of the considered cell has lower dimensions. From the derivative of the grey value as the cell goes by, the punctual value of the grey value along a horizontal section of the cell can be calculated, with a horizontal resolution equal to the number of points during the acquisition, and vertical resolution equal to the gap (distance) between the electrodes.

Based on what above described, it is therefore apparent that the invention also allows to characterize particles (BEADS) (that is, for example, to establish their physical nature) present in points of stable equilibrium (PEQ) of a force field (F) acting on the particles and generated by an array of electrodes (EL), through the carrying out of the following steps:
a. modifying the force field (F) so as to displace said points of stable equilibrium (PEQ) by passing said particles (BEADS) in correspondence with respective sensors (PIXEL_IJ);
b. measuring the grey level detectable by the sensors (PIXEL_IJ) associated with the transit of different points of stable equilibrium (PEQ) containing particles, with a frequency substantially higher than the settling time of the particles in the new equilibrium position;
c. processing characteristic parameters of the temporal evolution of the grey level measurement for estimating the nature of the particles.

The whole always without being affected from the background "noise" detectable by the sensors, namely the Fixed Pattern Noise.

In the described example, where the sensors used are optical sensors and the measurement of the grey level is a measurement of the optical power striking on the sensors, such measurement preferably takes place by alternating the steps of
i. activating the field acting on the particle;
ii. deactivating the field and measuring the incident optical power; or by using the same preferred system above described for the dynamic detection of the presence of particles in the cages. The parameters of the temporal evolution of the measurement of the optical power include, based on what above described, at least one of the parameters selected from the group consisting of:
i. the delay (td) between the variation of the force field (F) and the first variation of the optical power
ii. the length (tw) of the transitory variation of the optical power;
iii. the amplitude of the positive peak (Gpp) of the optical power value;
iv. the amplitude of the negative peak (Gnp) of the optical power value.

Method for the Counting of Different Species of Cells in an Heterogeneous Sample By combining the methodologies for the counting of cells for a single population with the characterization of the particles in the single cages it is possible, according to the present invention, to determine the composition of a sample with heterogeneous types of particles.

Generally, it is not easy to differentiate the composition of particles in cages which contain more than one cell. However, by processing the dynamic of the grey level, recorded as above described for the characterization of the content of a cage, it is relatively simple to determine if the cage contains a single particle or a multiplicity of particles (MC).

Figure 21:
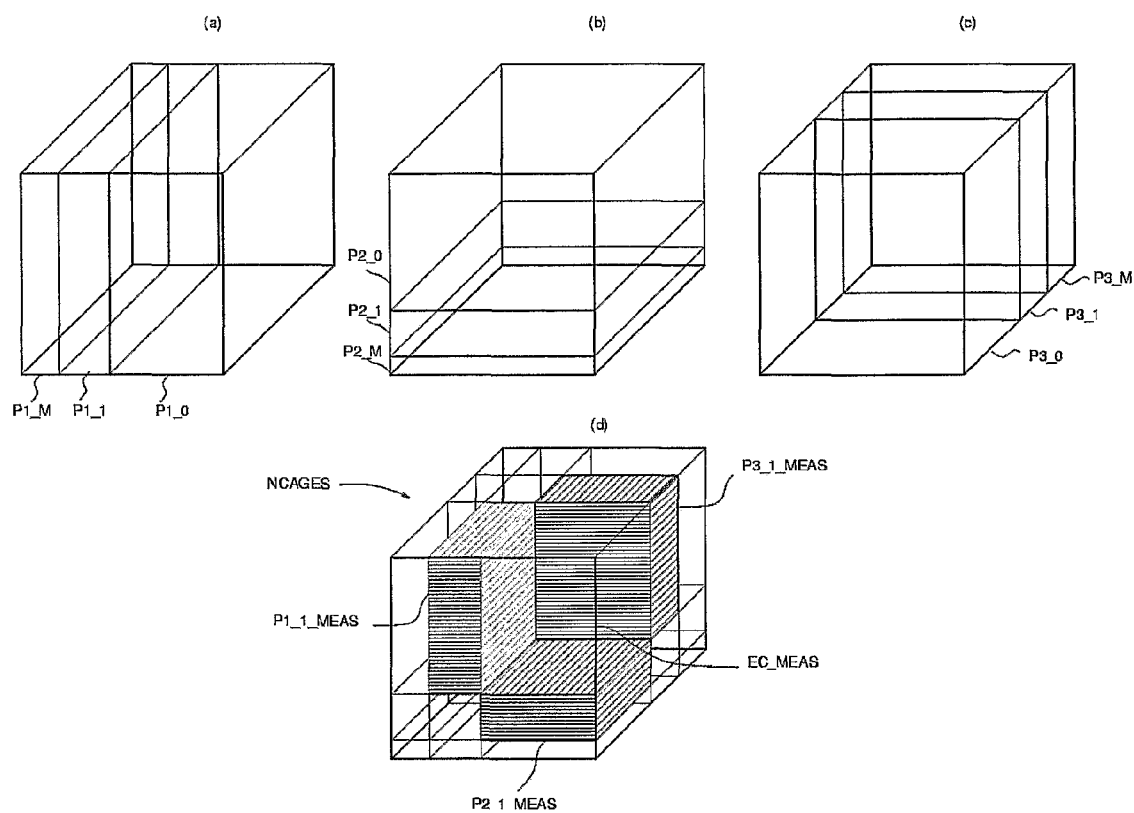
FIG. 21 shows a geometrical representation of the counting of different types of particles, particularly of three different types.

Since it can be assumed that the distribution of different types of particles are independent (orthogonal) therebetween, by combining the number of particles of each type obtained in the cages with a single particle, and the information relating to the number of empty cages (EC) and the total number of cages, it is therefore possible to determine the estimation of the number of particles of the different populations, by a numerical route. The problem is the minimization of a function with varying NPT (where NPT=number of types of particles). In FIG. 21 a representation of the problem in case of NPT=3 is reported.

For each type of particle t=1, . . . NPT, once the presence of a number of particles (NCELLSt) has been supposed, the volume of the hypercube of the space to NPT dimensions which represents the number of particles of the t type existing in a cage alone (by ignoring the other kinds of particles), remains in fact fixed (Pt_1). With reference to the FIG. 21(a), for the particles of a first type, we will obtain P1_1 particles in a single cage, P1_M particles in multiple cages and P1_0 cages without particles of the type P1 (the measures of the shown volumes). The detected number of t-type particles in a single cage must take into account, however, that one or more particles of other types can be present in the same cages. Therefore, as shown in FIG. 21(d), the detected value of single particles (Pt_1_MEAS) of each type t corresponds to the volume (Pt_1) of the hypercube of particles of type t minus the volume of the intersection hypercubes between Pt_1 and Pq_h, with q< >t and h>0 of hypercubes which contain at least a particle of a different type. The volume of the hypercube of empty cages (EC_MEAS) is further known.

The tuple of values NCELLSt, t=1, . . . , NTP is calculated by numerical way, whereby the (statistically) expected value better corresponds to the actually measured number (Pt_1) of cages with a single particle of each type t and of empty cages (EC_MEAS).

Based on what just described, it is therefore apparent that the invention also allows to count the number of particles (BEADS) of a multiplicity of types (NTP), existing in points of stable equilibrium (PEQ) of a force field (F) acting on the particles and generated by an array of electrodes (EL), through the execution of the following steps:
a. modifying the force field (F) so as to displace said points of stable equilibrium (PEQ) by passing said particles (BEADS) in correspondence with respective sensors (PIXEL_IJ);
b. measuring the grey level detectable by the sensors (PIXEL_IJ) associated with the passage of the different points of stable equilibrium (PEQ) containing particles, with a frequency substantially higher than the settling time of the particles in the new equilibrium position;
c. processing characteristic parameters of the temporal evolution of the grey level measure associated with each point of stable equilibrium (PEQ) for detecting if the associated cage is empty, if it contains a particle of a type or if it contains more particles;
d. determining in a numerical way the combination of countings of particles of each type (NCELLSt) which better approximates to the measured value of cages with a single particle of each type (Pt_1_MEAS) and empty cages (EC_MEAS).

Apparatus for the High Resolution Characterization of the Cells in the Cages Through Movement of the Cages and Measurement of the Dynamic Value of the Grey Level.

Figure 15:
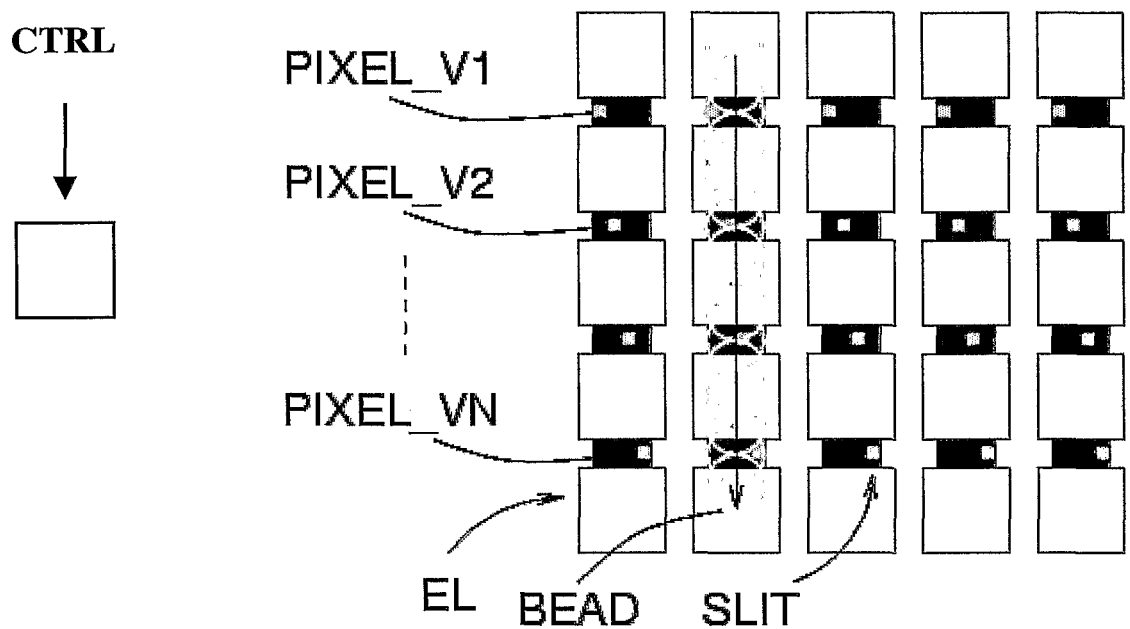
FIG. 15 shows the architecture of a device for the high resolution investigation of the features of the particles.

In order to increase the resolution of the dynamic detection methods described so far, according to the present invention it is possible to combine (FIG. 15) a series of electrodes (EL) associated with photodiodes (PIXEL_V1, . . . PIXEL_VN) characterized by a greater spatial resolution, to sequentially analyze different sections of the particle, by sequentially moving it on different electrodes.

The resolution limit is thus determined by the minimal geometry of the photolithographic resolution and it does not have the need of placing different transistors for the addressing of the electrodes (pixels), which would increase the required area. For example, some openings (SLITS) can be carried out on a metallizing arranged upon the photodiode, so as to render it sensitive only in correspondence with the same opening.

In this way, a further step can be implemented in all the methods described so far, in which said points of stable equilibrium (PEQ) are displaced such that said particles (BEADS) are passed in correspondence with a plurality of respective said sensors (PIXEL_IJ); and in which the sensors (PIXEL_IJ) are optical sensors and are shielded (through the aforesaid metallizing layer equipped with openings SLITS of a pre-fixed and relatively small amplitude), so as to detect with the sensors the incident optical power on a space portion substantially lower than the dimensions of the particles and the sensors themselves.

Method for the Manipulation of Cells with an Automatic Control of the Displacement Speed of the Cages A method of manipulation with an automatic control of the displacement speed of the cages can then be based on the use of the passage detection of the cells, as above described. For the cages with cells which are moving on the chip (together with the array of electrodes) the evolution of the grey levels can be monitored and the end of the settling transient in the new point of equilibrium can be detected for immediately starting the following step along the trajectory. Besides the optimization of the times, by dynamically adapting them to the speed of the different particles in the different moments, such approach also allows to verify that each cell does not remain blocked.

If to each electrode a single optical sensor is associated, for example in the vertical gap (distance) between two electrodes, as in FIG. 4, this method cab be carried out using cages with a width of 1×2 electrodes (1 in a horizontal position×2 in a vertical position). In the horizontal displacement, in fact, the particle locates itself at full speed on the sensor between the two electrodes, and its movement can be followed by monitoring the sensor in correspondence with the initial and/or final point of equilibrium. This introduces a bond on the cage shape, which however can be overcome by using an apparatus as described below.

Apparatus for the Manipulation of Cells with Automatic Control of the Displacement Speed of the Cages, without Bonds on the Dimensions of the Same.

Figure 16:
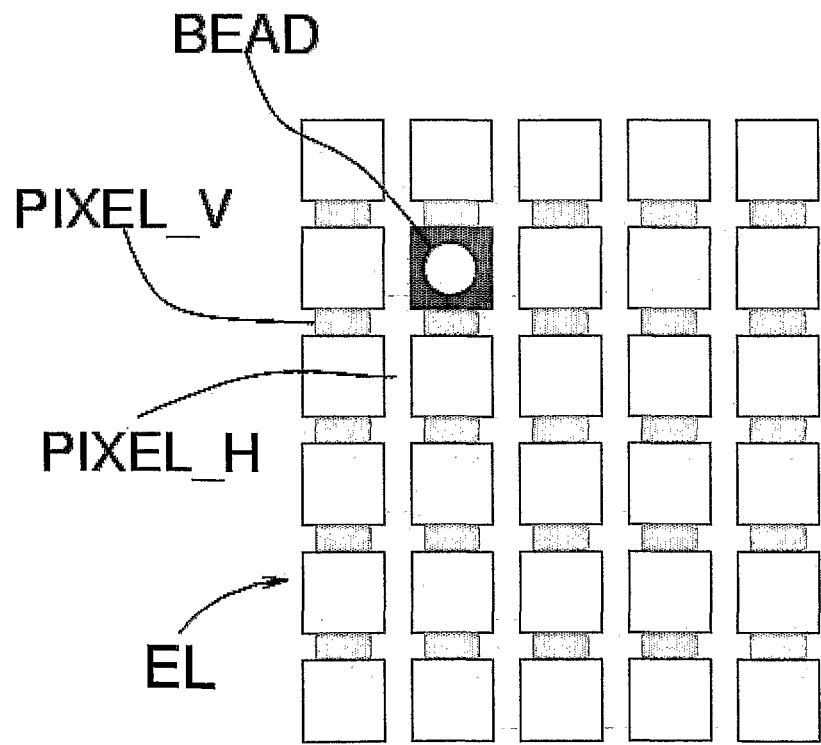
FIG. 16 shows the architecture of a device for the real-time determination of the displacement of the particles both in the vertical and the horizontal direction.

In FIG. 16, the diagram of an apparatus with sensors (pixels) for the movement determination both in horizontal (PIXEL_H) and in vertical (PIXEL_V) direction is shown. Such apparatus is advantageous for implementing a manipulation of particles with a close chain control, carried out in an integrated manner with the one of the displacement speed of the cages. With this apparatus, the horizontal displacement also with cages 1×1 can be carried out, since the cell/particle passes in any case on the sensor (PIXEL_H) placed between two electrodes along the horizontal axis.

With the additional method and apparatus now described, a step applicable on all the methods of detection and characterization of particles above described is implemented, consisting of the control of the variation course in the grey level detectable by the sensors (PIXEL_IJ) associated with the passage of the points of stable equilibrium (PEQ) containing particles, so as to determine the end of the settling transient of the particles in the new position of equilibrium and go back from this measure to the displacement speed of the particles (BEADS) towards new points of stable equilibrium (PEQ). At the end of such a settling transient, a variation in the force field (F) produced by the electrodes themselves can be therefore automatically generated (for example through a proper software implemented in a control unit CTRL, moreover of a known type, of the array of electrodes EL (FIG. 15), for the purpose of causing a new displacement of the points of stable equilibrium (PEQ) along the pre-fixed desired trajectory (shown in FIG. 15 by the arrow).

Apparatus with Integrated Dichroic Filters for the Detection and/or the Characterization of the Cells in the Cages by Means of Fluorescence For the fluorescence detection and/or the characterization of cells, some preferred implementations according to the present invention are reported. These implementations integrate a filter element which allows the passage of the fluorescence emission but mitigates the excitation. These filter elements can be integrated with process steps downstream of the chip execution, such as thin film depositions of materials with opportune indexes of refraction for carrying out dichroic filters. The filter effect allows to mitigate the part of optical power in the excitation band detected by the sensor (PIXEL), thus reducing the requirements bound to the dynamic range of the sensor itself.

Figure 18:
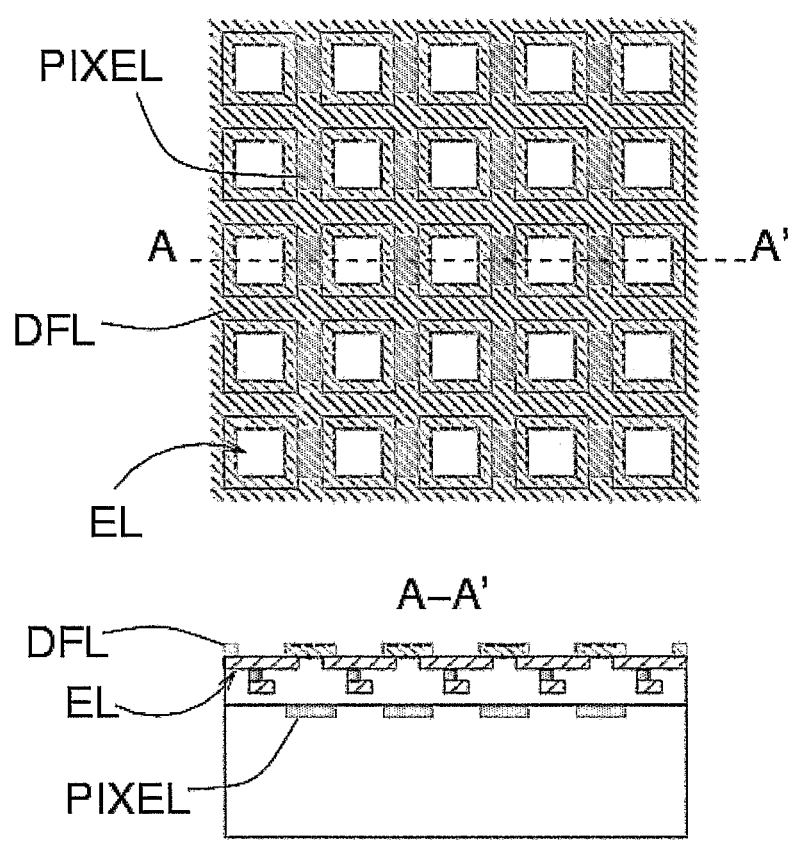
FIG. 18 shows the top and the sectional view of a special device for promoting the detection of fluorescent cells, with an emission filter integrated on the chip surface.

In FIG. 18, the diagram of an apparatus particularly suitable for the detection and/or characterization of fluorescence cells is shown. A dichroic filter (DFL) which allows the passage of the frequencies corresponding to the emission is deposited, with techniques known to those skilled in the art, on the chip. After the deposition, optionally, wishing to improve the electric contact between an electrode (EL) and a liquid, some windows on the dichroic layer are opened, in correspondence with the electrodes themselves. In this way, it is possible, for example, to use even high conductive solutions, in case of electrophoresis, without voltage drops connected with the presence of the dielectric layer composed of the dichroic filter. This execution scheme is compatible with the use of a standard CMOS wafer manufacture and only involves a post-processing of the wafers.

Figure 19:
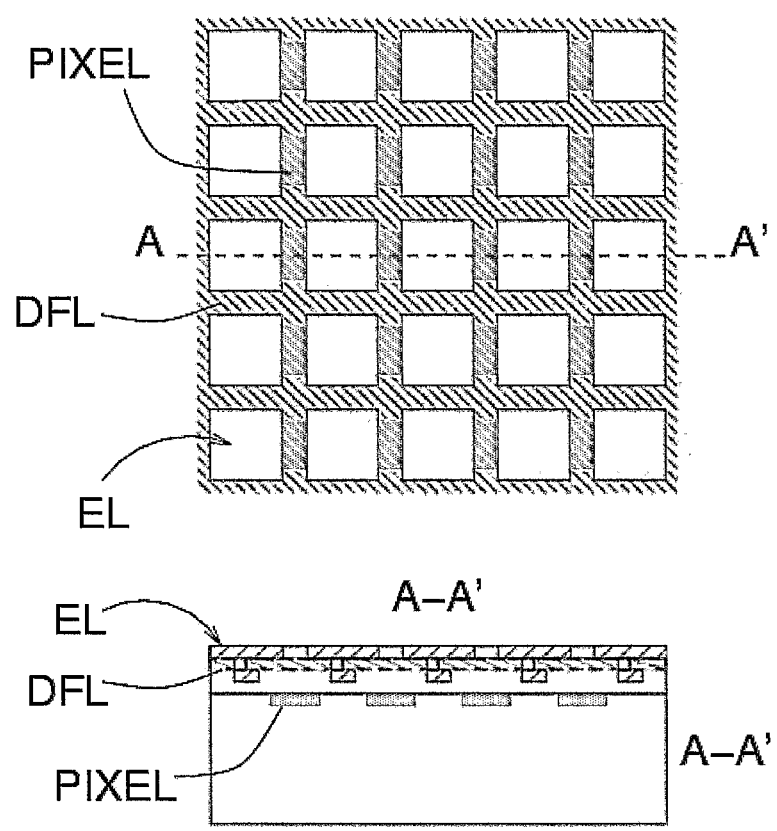
FIG. 19 shows the top and the sectional view of a special device for promoting the detection of fluorescent cells, with an emission filter integrated on the internal layers of the chip.
Figure 20:
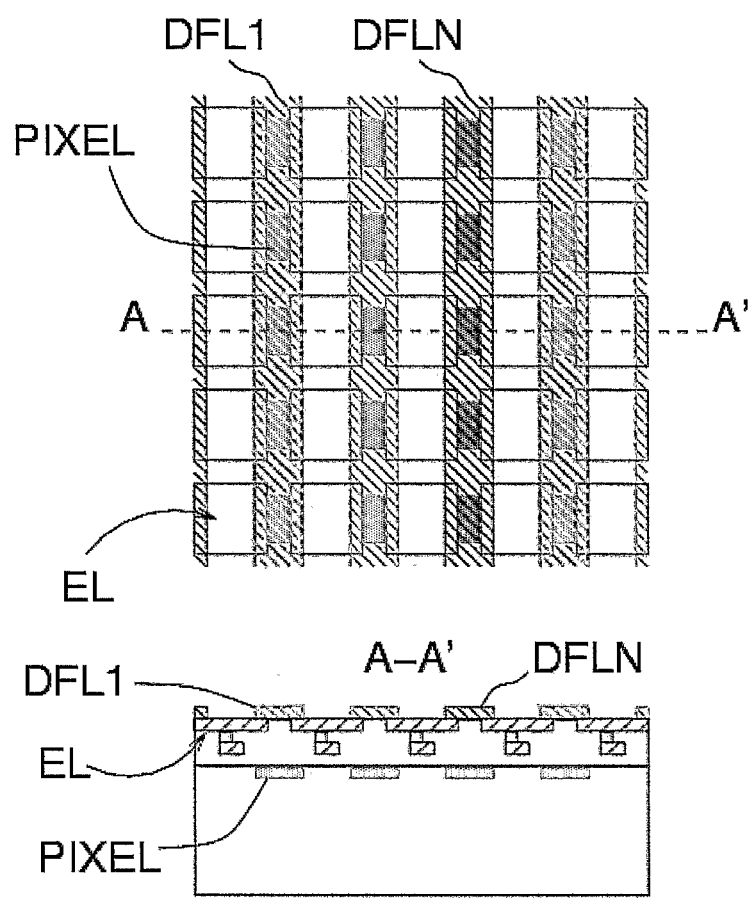
FIG. 20 shows the top and the sectional view of a special device for promoting the detection of fluorescent cells, with multiple emission filters integrated on the chip surface.

Alternatively, the dichroic filter can be carried out below the electrodes, as it is shown in FIG. 19. This can be useful if the CMOS process can be modified. Also without the modification of the CMOS process, this diagram can be however carried out by performing a post-processing, even if more complex, represented by the application of the filter, the opening of contacts at the CMOS top metal and the additional metallizing for carrying out the electrodes (EL). It can be advantageous to carry out, regardless by the fact of being above or below the electrodes (EL), a spatially organized multiplicity of dichroic filters with a different passband (DFL1, DFLN), as it is shown in FIG. 20. This can be useful for dividing and separately detecting the fluorescence of cells/particles at different emission frequencies.

Clearly, by checking the cells position it is then possible to analyze them in sequence, on different sensors, for the presence for example of different fluorophores. According to this aspect of the invention just described, the invention relates to an apparatus for the detection and/or characterization of particles as above described, but further including shielding means of the sensors and openings, in a number of at least one for each sensor, obtained through the shielding means and having pre-fixed dimensions, smaller than those of the particles to be detected/characterized.

The apparatus according to the invention can further include at least a dichroic filer with a pre-fixed passband arranged such that it shields at least partly the sensors (PIXEL), if these are optical sensors, and preferably include a plurality of dichroic filters, each having a passband different from the others, arranged superimposed therebetween and so as to shield however at least partly the sensors (PIXEL). If at least a dichroic filter is arranged to cover the electrodes (EL), it is equipped with interruption openings placed in correspondence with at least part of each electrode.

Filtering of the Excitation

The apparatus can take advantage, or not, of the fact that (externally) the excitation source is filtered and optimized for each fluorophore to be analyzed. This can be easily carried out with filters non integrated on the device. Furthermore, or alternatively, the lid of the chip can integrate the part of the excitation filtering corresponding with underlying dichroic filters, which vary, or not, from pixel to pixel of the chip.

If the excitation filtering is integrated on the lid, it is necessary to carry out wider zones with a homogeneous dichroic filter, so as to avoid cross-talk between the excitations of the different pixels. In this case, the cell under test must cover a greater distance for being analyzed for different fluorophores. According to this additional aspect of the invention, the apparatus described so far can therefore include at least a dichroic filter with a pre-fixed passband arranged in correspondence with the cover (LID) defining, together with the array of electrodes (EL), a chamber or micro-chamber suitable for receiving and containing a fluid sample containing the particles to be detected/characterized.

Compensation Method of the Illumination Noise

In all the methods above mentioned, when optical sensors are used, the signal for the detection or the characterization of the particles depends on the illumination power. Therefore, variations of this type can cause some variations of the level of the optical power detected which are not bound to the signal (presence and/or position of the particle). Although normally this is not a problem, the performances of the methods (greater precision, greater speed) can be however improved, compensating such variations by using a value normalized to the average detection of the reference pixels (pixels certainly corresponding with empty cages, for which the optical incident power is only affected by the illumination power).

This is mainly true for the low-frequency illumination noise, which because of the spectral density of the noise power (proportional to 1/f, makes the impact thereof more influent.

Method of Noise Compensation for Impedance Sensors.

In all the methods above mentioned, when impedance meter sensors are used, the signal for the detection and the characterization of the particles depends on the conductivity and permittivity of the suspension medium of the particles, which in turn depends for example on the temperature, the salts concentration or other molecules, etcetera. Therefore, variations of these can cause some variations of the level of the detected impedance which are not bound to the signal (presence and/or position of the particle). Although normally this is not a problem, the performances of the methods (greater precision, greater speed) can be however improved, compensating such variations by using a value normalized to the average detection of the reference pixels (pixels certainly corresponding with empty cages, for which the impedance is only affected by the conductivity and the permittivity of the suspension medium).

In all the methods of detection and characterization described so far, a further step consisting of a compensation of the grey levels detected by said sensors (PIXEL_IJ) can therefore be introduced, using a value normalized to the average detection of reference sensors (PIXEL_REF) associated with space regions which can not certainly be occupied by particles in the current configuration of the considered force field (F).

Note on the Applications

The methods and the apparatus described so far are of a general use and find multiple applications. By way of example but not limitation of the invention, we mention some of the most important applications:

Analysis of blood samples; by introducing a sample on the chip (which uses for example closed dielectrophoresis cages) the red cells can be counted by counting as a first approximation all the occupied cages (in fact the other cells possibly existing have a so lower concentration that it results negligible for the precision typically required).

Emochroma: characterization of the number and type of cells in the blood; in this case, the method above described for carrying out an accurate characterization of each single existing cell is employed, by classifying it as a red cell, platelet lymphocyte, etcetera.

Counting of the bacteria existing in a sample; by injecting on the chip (with DEP closed cages) a known volume of sample, all the bacteria existing are detected, and if necessary also the type, if they are distinguishable through their characteristic signature detected with the optical sensors.

Separation/counting of the cells labelled with fluorescence from a mixed population. This type of problem is widely diffuse both in the research and the diagnostics.

For example, bacteria in dairy samples, such as milk, yoghurt, ice-cream preparations, etcetera can be detected.

As another example, bacteria for a fermentation of grape must (for example for enological applications) can be detected.

As a further example, bacteria existing in a volume of drinking water could be detected.

The invention claimed is:

1. Method for the detection of the presence of particles (BEADS) possibly present in points of stable equilibrium (PEQ) of a force field (F) acting on said particles, generated by an array of electrodes (EL), comprising the steps of:
   i. deactivating the force field (F);
   ii. measuring, in at least a time interval following the deactivation, a grey level generated by first sensors (PIXEL_IJ) associated with said stable equilibrium points (PEQ) and by second sensors (PIXEL_REF) associated with space regions not occupied by particles because of the current configuration of said force field (F), wherein the time interval is a function of a dynamic of settling and/or Brownian movements to which the particles are subjected with the deactivating of the force field;
   iii. reactivating the force field (F);
   iv. repeating the steps from i) to iii) a number of times, wherein the number of times is substantially comparable with convergence rate, of the variance of the grey level measured on said second sensors to its asymptotic value;
   v. classifying a point of equilibrium as occupied by particles if, in the considered temporal series of measurements, the standard deviation of the grey level measured on the first sensors is higher than a pre-fixed threshold (THR).

2. Method according to claim 1, characterized in that said threshold (THR) corresponds to the average value of the grey level detected on said second sensors increased by a factor proportional to the standard deviation of the grey level detected on said second sensors (PIXEL_REF).

3. Method for the detection of the presence of particles (BEADS) possibly existing in points of stable equilibrium (PEQ) of a force field (F) acting on said particles, generated by an array of electrodes (EL), comprising the steps of:
  i. measuring a grey level generated by first sensors (PIXEL_STA) associated with said points of stable equilibrium (PEQ), and by reference sensors (PIXEL_REF) associated with space regions not occupied by particles in a first current configuration of said force field (F);
  ii) modifying said force field (F) in order to impart it a second current configuration wherein said stable equilibrium points are displaced in correspondence with second sensors (PIXEL_TGT), different from the first sensors;
  iii) measuring a grey level generated by the second sensors (PIXEL_TGT) and by reference sensors (PIXEL_REF) associated with space regions not occupied by particles in said second current configuration of said force field (F);
  iv) determining the difference (DIFF_IMG) between the grey level detected in steps i) and iii);
  v) repeating the steps i) to iv);
  vi) processing differential grey level values in order to classify the points of stable equilibrium (PEQ) occupied by particles and those not occupied.

4. Method according to claim 3, characterized in that such processing includes the steps of determining the absolute value of the differences in grey levels, and classifying as occupied the points of equilibrium associated to sensors for which a variation substantially higher than the average variation of the grey level associated with said reference sensors which can not be occupied by particles in said first and second configurations of the force field (F) is detected.

5. Method for the detection of the presence of particles (BEADS) possibly existing in points of stable equilibrium (PEQ) of a force field (F) acting on said particles, generated by an array of electrodes (EL), comprising the steps of:
  i. modifying said force field (F) so as to displace said points of stable equilibrium (PEQ) to get said particles (BEADS) pass in correspondence with respective sensors (PIXEL_IJ);
  ii. measuring a grey level generated by sensors (PIXEL_IJ) associated with the passage of said different points of stable equilibrium (PEQ), with a frequency substantially higher than the settling time of said particles in the new equilibrium position;
  iii. classifying the presence or the absence of particles through the measurement of at least a characteristic parameter of the temporal evolution of the grey level measured by said sensors (PIXEL_IJ).

6. Method of claim 5, characterized in that said characteristic parameter of the temporal evolution of the measurement of the grey levels on said sensors (PIXEL_IJ) comprises the peak to peak amplitude.

7. Method of claim 5, characterized in that the classification takes place through the comparison with a threshold value determined starting from peak to peak measurements of the grey levels on reference sensors which cannot be occupied by particles with the configuration of the considered force field (F), increased by a factor proportional to the standard deviation of said peak to peak values of said reference sensors.

8. Method of claim 5, further including a counting step of the total number of particles of which the presence has been detected, characterized in that said counting step takes place in a way estimated on statistical bases, in the following way:
  i. the number ($EC_{measure}$) of points of stable equilibrium (PEQ) existing in the field (F) generated by the array of electrodes (EL), which do not contain any particle (BEAD), is measured by the sensors;
  ii. the counting (NCELLS) of particles (BEADS) is determined as the ratio of the difference of the logarithm of the number (NCAGES) of points of stable equilibrium (PEQ) to the logarithm of the measured number ($EC_{measure}$) of the points of stable equilibrium (PEQ) non containing any particle, and the difference of the logarithm of the number (NCAGES) of points of stable equilibrium (PEQ) to the logarithm of the number (NCAGES-1) of the points of stable equilibrium (PEQ) less one.

9. Method for the characterization of particles (BEADS) existing in points of stable equilibrium (PEQ) of a force field (F) acting on said particles, generated by an array of electrodes (EL), comprising the steps of:
  i. modifying said force field (F) so as to displace said points of stable equilibrium (PEQ) by passing said particles (BEADS) in correspondence with respective sensors (PIXEL_IJ);
  ii. measuring a grey level generated by sensors (PIXEL IJ) associated with the passage of the different points of stable equilibrium (PEQ) containing particles, with a frequency substantially higher than the settling time of said particles in the new position of equilibrium;
  iii. processing characteristic parameters of the temporal evolution of the grey level measurement in order to estimate the nature of said particles.

10. Method of claim 9, characterized in that said parameters of the temporal evolution of the grey level include at least one of the parameters selected from the group consisting of:
  i. the delay (td) between the variation of the force field (F) and the first variation of the grey level;
  ii. the length (tw) of the transitory variation of the grey level;
  iii. the width of the positive peak (Gpp) of the grey level;
  iv. the width of the negative peak (Gnp) of the grey level.

11. Method for counting the number of particles (BEADS) of a multiplicity of types (NTP), existing in points of stable equilibrium (PEQ) of a force field (F) acting on said particles and generated by an array of electrodes (EL), comprising the following steps:
  i. modifying the force field (F) so as to displace said points of stable equilibrium (PEQ) by passing said particles (BEADS) in correspondence with respective sensors (PIXEL_IJ);
  ii. measuring a grey level detectable by the sensors (PIXEL_IJ) associated with the passage of the different points of stable equilibrium (PEQ) containing particles, with a frequency substantially higher than the settling time of the particles in the new position of equilibrium;
  iii. processing characteristic parameters of the temporal evolution of the grey level measurement associated with each point of stable equilibrium (PEQ) for detecting if the associated cage is empty, if it contains a particle of a type or if it contains more particles;
  iv. determining in a numerical way the combination of countings of particles of each type (NCELLSt) which better approximates to the measured value of cages with a single particle of each type (Pt_1_MEAS) and empty cages (EC_MEAS).

12. Method of claim 11, characterized in that said points of stable equilibrium (PEQ) are displaced such that said particles (BEADS) are passed in correspondence with a plurality of respective sensors (PIXEL_IJ); and in that said sensors (PIXEL_IJ) are optical sensors and are shielded so as to detect the incident optical power on a portion of space substantially lower than the dimensions of the particles.

13. Method of claim 12, characterized in that the course of the variation in the grey level detectable by the sensors (PIXEL_IJ) associated with the transit of said points of stable equilibrium (PEQ) containing particles is controlled, so as to determine the end of the settling transient of said particles in the new equilibrium position and go back from this measurement to the displacement speed of said points of stable equilibrium (PEQ).

14. Method of claim 13, characterized in that at the end of said settling transient, a variation in said force field (F) is produced for causing a new displacement of said points of stable equilibrium (PEQ).

15. Method of claim 1, characterized in that said sensors are optical sensors and said grey level corresponds with the optical power striking on the sensors.

16. Method of claim 1, characterized in that said sensors are impedance meter sensors.

17. Method of claim 1, characterized in that a compensation of the values of the grey levels detected by said sensors (PIXEL_IJ) is carried out using a value normalized to the average detection of reference sensors (PIXEL_REF) associated with space regions which cannot certainly be occupied from particles in said current configuration of said force field (F).

18. Method of claim 1, characterized in that said measurement of the grey level takes place by temporarily deactivating said force field (F).

19. Method of claim 1, characterized in that said force field (F) is generally selected from: positive dielectrophoresis, negative dielectrophoresis, Electrowetting on dielectric, electrohydrodynamic flows, electrophoresis.

20. A method for the detection and/or characterization of particles (BEADS) comprising
generating points of stable equilibrium (PEQ) of a force field (F) acting on said particles by an array of electrodes (EL);
providing sensors (PIXEL) associated with said electrodes; and
displacing said points of stable equilibrium (PEQ) in correspondence with said optical sensors (PIXELS) and/or letting said particles to be displaced in correspondence with said optical sensors (PIXELS),
wherein to each said electrode (EL) a first sensor (PIXEL_V) for detecting the transit of said particles in a vertical direction, and a second sensor (PIXEL_H) for detecting the transit of said particles in a horizontal direction are provided.

21. The method of claim 20, comprising providing at least a dichroic filter with a pre-fixed passband arranged so as to shield at least partly said sensors (PIXEL), wherein the sensors are optical sensors.

22. The method of claim 21, comprising providing a plurality of dichroic filters, each having a passband selected from a set of different passbands, arranged in a non-superimposed way between them and so as to shield in any case at least partly said sensors (PIXEL).

23. The method of claim 21, wherein said at least a dichroic filter is arranged to cover said electrodes (EL) and is equipped with interruption openings placed in correspondence with at least part of each said electrode.

24. The method of claim 20, comprising providing at least a dichroic filter with a pre-fixed passband arranged in correspondence with a cover (LID) defining together with said array of electrodes (EL) a chamber or a micro-chamber suitable for receiving and containing a fluid sample containing said particles.

* * * * *